US011578135B2

(12) United States Patent
Papadopoulos et al.

(10) Patent No.: US 11,578,135 B2
(45) Date of Patent: Feb. 14, 2023

(54) MULTISPECIFIC ANTIGEN-BINDING MOLECULES BINDING TO A TARGET AND AN INTERNALIZING EFFECTOR PROTEIN THAT IS CD63 AND USES THEREOF

(71) Applicant: Regeneron Pharmaceuticals, Inc., Tarrytown, NY (US)

(72) Inventors: Nicholas J. Papadopoulos, The Woodlands, TX (US); Andrew J. Murphy, Croton-on-Hudson, NY (US); Aris N. Economides, Tarrytown, NY (US); Katherine Diana Cygnar, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 388 days.

(21) Appl. No.: 16/394,849

(22) Filed: Apr. 25, 2019

(65) Prior Publication Data

US 2019/0309061 A1 Oct. 10, 2019
US 2021/0115132 A9 Apr. 22, 2021

Related U.S. Application Data

(63) Continuation of application No. 13/798,205, filed on Mar. 13, 2013, now abandoned.

(60) Provisional application No. 61/751,286, filed on Jan. 11, 2013, provisional application No. 61/721,831, filed on Nov. 2, 2012, provisional application No. 61/610,494, filed on Mar. 14, 2012.

(51) Int. Cl.
| | | |
|---|---|---|
| *C07K 16/28* | (2006.01) | |
| *C07K 16/22* | (2006.01) | |
| *C07K 16/12* | (2006.01) | |
| *A61K 39/395* | (2006.01) | |
| *A61K 47/68* | (2017.01) | |
| *C07K 14/705* | (2006.01) | |
| *C07K 14/715* | (2006.01) | |
| *C07K 14/475* | (2006.01) | |
| *A61P 19/08* | (2006.01) | |
| *A61P 35/00* | (2006.01) | |
| *C07K 16/30* | (2006.01) | |
| *C07K 16/16* | (2006.01) | |

(52) U.S. Cl.
CPC ...... *C07K 16/2896* (2013.01); *A61K 39/3955* (2013.01); *A61K 47/6817* (2017.08); *A61K 47/6879* (2017.08); *C07K 16/1203* (2013.01); *C07K 16/22* (2013.01); *C07K 16/2866* (2013.01); *A61P 19/08* (2018.01); *A61P 35/00* (2018.01); *C07K 14/475* (2013.01); *C07K 14/705* (2013.01); *C07K 14/70596* (2013.01); *C07K 14/7155* (2013.01); *C07K 16/16* (2013.01); *C07K 16/28* (2013.01); *C07K 16/283* (2013.01); *C07K 16/2833* (2013.01); *C07K 16/2851* (2013.01); *C07K 16/2863* (2013.01); *C07K 16/2869* (2013.01); *C07K 16/30* (2013.01); *C07K 2317/31* (2013.01); *C07K 2317/77* (2013.01); *C07K 2317/94* (2013.01)

(58) Field of Classification Search
CPC ................ C07K 16/28; C07K 2317/31; C07K 2317/77; C07K 16/2896; C07K 16/2866; C07K 16/22; C07K 16/1203; A61K 39/3955; A61K 47/6879
See application file for complete search history.

(56) References Cited

U.S. PATENT DOCUMENTS

| | | | |
|---|---|---|---|
| 4,444,878 | A | 4/1984 | Paulus |
| 4,975,278 | A | 12/1990 | Senter et al. |
| 5,030,717 | A | 7/1991 | Tramontano et al. |

(Continued)

FOREIGN PATENT DOCUMENTS

| | | |
|---|---|---|
| JP | 2008-506659 | 3/2008 |
| WO | 1998/016254 A1 | 4/1998 |

(Continued)

OTHER PUBLICATIONS

Benjamini et al, 1991. Immunology: A Short Course, 2nd edition, p. 40 only.*

(Continued)

*Primary Examiner* — Zachary C Howard
(74) *Attorney, Agent, or Firm* — Rita S. Wu; FisherBroyles, LLP; Todd R. Samelman

(57) ABSTRACT

The present invention provides multispecific antigen-binding molecules and uses thereof. The multispecific antigen-binding molecules comprise a first antigen-binding domain that specifically binds a target molecule, and a second antigen-binding domain that specifically binds an internalizing effector protein. The multispecific antigen-binding molecules of the present invention can, in some embodiments, be bispecific antibodies that are capable of binding both a target molecule and an internalizing effector protein. In certain embodiments of the invention, the simultaneous binding of the target molecule and the internalizing effector protein by the multispecific antigen-binding molecule of the present invention results in the attenuation of the activity of the target molecule to a greater extent than the binding of the target molecule alone. In other embodiments of the invention, the target molecule is a tumor associated antigen, and the simultaneous binding of the tumor associated antigen and the internalizing effector protein by the multispecific antigen-binding molecule of the present invention causes or facilitates the targeted killing of tumor cells.

14 Claims, 9 Drawing Sheets

Specification includes a Sequence Listing.

(56) References Cited

U.S. PATENT DOCUMENTS

| | | | |
|---|---|---|---|
| 5,126,258 | A | 6/1992 | Lerner et al. |
| 5,156,965 | A | 10/1992 | Schochetman et al. |
| 5,229,272 | A | 7/1993 | Paul et al. |
| 5,436,153 | A | 7/1995 | Sprecher et al. |
| 5,601,819 | A | 2/1997 | Wong et al. |
| 5,602,021 | A | 2/1997 | Davis et al. |
| 5,851,527 | A | 12/1998 | Hansen |
| 5,858,728 | A | 1/1999 | Gram et al. |
| 6,235,714 | B1 | 5/2001 | Paul et al. |
| 6,372,205 | B1 | 4/2002 | Duncan et al. |
| 6,387,674 | B1 | 5/2002 | Trasciatti et al. |
| 6,479,265 | B1 | 11/2002 | Napper et al. |
| 6,703,488 | B1 | 3/2004 | Burton et al. |
| 6,855,804 | B2 | 2/2005 | Paul et al. |
| 7,041,298 | B2 | 5/2006 | Deshaies et al. |
| 7,087,411 | B2 | 8/2006 | Daly et al. |
| 7,105,348 | B2 | 9/2006 | Murphy et al. |
| 7,223,556 | B1 | 5/2007 | Zhou et al. |
| 7,235,641 | B2 | 6/2007 | Kufer et al. |
| 7,335,504 | B2 | 2/2008 | Haupts et al. |
| 7,371,539 | B2 | 5/2008 | Church et al. |
| 7,431,923 | B2 | 10/2008 | Young et al. |
| 7,442,777 | B2 | 10/2008 | Young et al. |
| 7,560,424 | B2 | 7/2009 | LeBowitz et al. |
| 7,592,429 | B2 | 9/2009 | Paszty et al. |
| 7,914,787 | B2 | 3/2011 | Goldenberg et al. |
| 8,058,399 | B2 | 11/2011 | Jung |
| 8,518,403 | B2 | 8/2013 | Hoffmann et al. |
| 9,738,717 | B2 | 8/2017 | Azorsa |
| 2005/0112694 | A1 | 5/2005 | Carter et al. |
| 2005/0271626 | A1 | 12/2005 | Chen et al. |
| 2006/0210474 | A1 | 9/2006 | Young et al. |
| 2007/0041978 | A1 | 2/2007 | Hatiori et al. |
| 2008/0044408 | A1 | 2/2008 | Young et al. |
| 2008/0089891 | A1 | 4/2008 | Hahn et al. |
| 2009/0155262 | A1 | 6/2009 | Young et al. |
| 2010/0081796 | A1 | 4/2010 | Brinkmann et al. |
| 2010/0233173 | A1 | 9/2010 | Wu et al. |
| 2010/0330034 | A1 | 12/2010 | Bigler et al. |
| 2012/0315276 | A1 | 12/2012 | Otto et al. |
| 2013/0022606 | A1 | 1/2013 | Otto et al. |
| 2013/0129739 | A1 | 5/2013 | Otto et al. |
| 2013/0171147 | A1 | 7/2013 | Otto et al. |
| 2013/0272968 | A1 | 10/2013 | Otto et al. |
| 2014/0065158 | A1 | 3/2014 | Ma et al. |
| 2014/0141003 | A1 | 5/2014 | Freiberg et al. |
| 2014/0271659 | A1 | 9/2014 | Ma et al. |
| 2014/0356366 | A1 | 12/2014 | Cheong et al. |
| 2015/0056221 | A1 | 2/2015 | Papadopoulos et al. |
| 2015/0056222 | A1 | 2/2015 | Papadopoulos et al. |
| 2015/0093393 | A1 | 4/2015 | Ma et al. |
| 2015/0252116 | A1 | 9/2015 | Ma et al. |
| 2015/0322149 | A1 | 11/2015 | Bohrmann et al. |
| 2016/0002342 | A1 | 1/2016 | Ma et al. |
| 2016/0115229 | A1 | 4/2016 | Azorsa |
| 2016/0251442 | A1 | 9/2016 | Papadopoulos et al. |
| 2016/0319029 | A1 | 11/2016 | Freiberg et al. |
| 2017/0007715 | A1 | 1/2017 | Andreev et al. |
| 2017/0008965 | A1 | 1/2017 | Ma et al. |
| 2018/0094066 | A1 | 4/2018 | Papadopoulos et al. |
| 2018/0185504 | A1 | 7/2018 | Kelly et al. |
| 2018/0355017 | A1 | 12/2018 | Baik et al. |
| 2019/0112588 | A1 | 4/2019 | Baik et al. |

FOREIGN PATENT DOCUMENTS

| | | |
|---|---|---|
| WO | 1999036437 A1 | 7/1999 |
| WO | 2001/009186 A1 | 2/2001 |
| WO | 2001036005 A2 | 5/2001 |
| WO | 2008/011710 A1 | 1/2008 |
| WO | 2008/011711 A1 | 1/2008 |
| WO | 2008/014404 A2 | 1/2008 |
| WO | 2008/019290 A2 | 2/2008 |
| WO | 2008/150485 A2 | 12/2008 |
| WO | 2009/094561 A1 | 7/2009 |
| WO | 2009/120922 A2 | 10/2009 |
| WO | 2010/119119 A1 | 10/2010 |
| WO | 2010115552 A1 | 10/2010 |
| WO | 2011/029823 A1 | 3/2011 |
| WO | 2011/069794 A1 | 6/2011 |
| WO | 2011/147986 A1 | 12/2011 |
| WO | 2012/136519 A1 | 10/2012 |
| WO | 2012/143379 A1 | 10/2012 |
| WO | 2012/143523 A1 | 10/2012 |
| WO | 2012/143524 A1 | 10/2012 |
| WO | 2013/166604 A1 | 11/2013 |
| WO | 2014/143909 A1 | 9/2014 |
| WO | 2014/185908 A2 | 11/2014 |
| WO | 2014182970 A1 | 11/2014 |
| WO | 2015/026907 A1 | 2/2015 |
| WO | 2015/187596 A2 | 12/2015 |
| WO | 2017/007796 A1 | 1/2017 |
| WO | 2017/190079 A1 | 2/2017 |
| WO | 2017/134197 A1 | 8/2017 |
| WO | 2018/102304 A1 | 6/2018 |
| WO | 2019/011719 A1 | 1/2019 |
| WO | 2019/212965 A1 | 11/2019 |

OTHER PUBLICATIONS

Horejsi et al, 1991. FEBS 288 1(2): 1-4.*
Drenth et al, 2007, The Journal of Clinical Investigation. 117(12): 3603-3609.*
Ferrara et al (2015. mAbs. 7(1): 32-41.*
Statement of Relatedness under MPEP 2001.06 with Respect to U.S. Appl. No. 16/394,849 dated Jul. 8, 2021.
Kontermann, "Dual targeting strategies with bispecific antibodies," mAbs, 2012, 4(2):182-197.
Phillips et al., "Dual Targeting of HER2-Positive Cancer with Trastuzumab Emtansine and Pertuzumab: Critical Role for Neuregulin Blockade in Antitumor Response to Combination Therapy," Clinical Cancer Research, 2014, 20 (2):456-468.
Ridgway et al., "'Knobs-into-holes' engineering of antibody CH3 domains for heavy chain heterodimerization," Protein Eng., 1996, 9(7):617-621.
Statement of Relatedness under MPEP 2001.06 with Respect to U.S. Appl. No. 16/394,849 dated Apr. 22, 2021.
Brissinck, J. et al. (1993). "Bispecific Antibodies in Lymphoma," Intern. Rev. Immunol. 10(2-3):187-94.
Schanzer, J.M. et al. (Jul. 2014). "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties," J. Biol. Chem. 289(27):18693-706.
Andreev et al., "Bispecific Antibodies and Antibody-Drug Conjugates (ADCs) Bridging HER2 and Prolactin Receptor Improve Efficacy of HER2 ADCs," Mol. Cancer Ther., Apr. 2017, 16(4):681-693.
Anzai et al., "c-kit associated with the transmembrane 4 superfamily proteins constitutes a functionally distinct subunit in human hematopoietic progenitors," Blood, 2002, 99(12):4413-4421, doi:10.1182/blood.V99.12.4413.
Arribas and Cutler, "Weibel-Palade Body Membrane Proteins Exhibit Differential Trafficking After Exocytosis in Endothelial Cells," Traffic, 2000, 1:783-793.
Bareford and Swaan, "Endocytic mechanisms for targeted drug delivery," Advanced Drug Delivery Reviews, Elsevier, Amsterdam, NL, 2007, 59(8):748-758.
Beatty et al., "Trafficking from CD63-positive late endocytic multivesicular bodies is essential for intracellular development of Chlamydia trachomatis," Journal of Cell Science, 2006, 119(2):350-359.
Berditchevski et al., "Specific Association of CD63 with the VLA-3 and VLA-6 Integrins," Journal of Biological Chemistry, 1995, 270(30):17784-17790.
Berditchevski et al., "Characterization of Novel Complexes on the Cell Surface between Integrins and Proteins with 4 Transmembrane Domains (TM4 proteins)," Molecular Biology of the Cell, 1996, 7:193-207.

(56) References Cited

OTHER PUBLICATIONS

Berditchevski et al., "A Novel Link between Integrins, Transmembrane-4 Superfamily Proteins (CD63 and CD81), and Phosphatidylinositol 4-Kinase*," Journal of Biological Chemistry, Jan. 1997, 272(5):2595-2598.

Berditchevski et al., "Generation of Monoclonal Antibodies to Integrin-associated Proteins," Journal of Biological Chemistry, Nov. 1997, 272(46):29174-29180.

Berditchevski et al., "Expression of the Palmitoylation-deficient CD151 Weakens the Association of α3β1 Integrin with the Tetraspanin-enriched Microdomains and Affects Integrin-dependent Signaling*," Journal of Biological Chemistry, 2002, 277(40):36991-37000.

Bode et al., "Antibody-Directed Fibrinolysis: An Antibody Specific for Both Fibrin and Tissue Plasminogen Activator," Journal of Biological Chemistry, Jan. 1989, 264(2):944-948.

Boersma et al., "DARPins and other repeat protein scaffolds: advances in engineering and applications," Curr. Opin. Biotechnol., 2011, 22:849-885.

Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.

Bostrom et al., "Variants of the Antibody Herceptin That Interact with HER2 and VEGF at the Antigen Binding Site," Science, 2009, 323(5921):1610-1614.

Bouilly et al., "Prolactin signaling mechanisms in ovary," Molecular and Cellular Endocrinology, 2012, 356:80-87.

Caplus Accession No. 1990:211724.

Clevenger and Kline, "Prolactin receptor signal transduction," 10(10) Lupus, (2001) 10:706-718.

De Goeij et al., "Efficient Payload Delivery by a Bispecific Antibody-Drug Conjugate Targeting HER2 and CD63," Mol. Cancer Ther., 2016, 15(11):2688-2697.

Devay et al., "Characterization of proprotein convertase subtilisin/kexin type 9 (PCSK9) trafficking reveals a novel lysosomal targeting mechanism via amyloid precursor-like protein 2 (APLP2)," J. Bioi. Chern., Apr. 2, 2013, 288(15):10805-10818, doi: 10.1074/jbc.M113.453373. Epub Feb. 19, 2013.

Devay et al., "Common Proprotein Convertase Subtilisin/Kexin Type 9 (PCSK9) Epitopes Mediate Multiple Routes for Internalization and Function," PLOS ONE, Apr. 23, 2015, 10(4):e0125127, 20 pages.

Devay et al., "Improved Lysosomal Trafficking Can Modulate the Potency of Antibody Drug Conjugates," Bioconjugate Chem., 2017, 28(4):1102-1114, DOI: 10.1021/acs.bioconjchem.7b00013.

Dipadova et al., "A Broadly Cross-Protective Monoclonal Antibody Binding to *Escherichia coli* and *Salmonella* Lipopolysaccharides," Infection and Immunity, Sep. 1993, 61(9):3863-3872.

Doyle et al., "CD63 is an essential cofactor to leukocyte recruitment by endothelial P-selectin," Blood, 2011, 118(15):4265-427.

Duffield et al., "The tetraspanin CD63 enhances the internalization of the H,K-ATPase β-subunit," Proc. Nail. Acad. Sci. USA, Dec. 2003, 100(26):15560-15565.

Egea et al., "Tissue inhibitor of metalloproteinase-1 (TIMP-1) regulates mesenchymal stem cells through let-7f microRNA and Wnt/β-catenin signaling," PNAS, 2012, 109(6):E309-E316.

Eigenbrot et al., "Structural basis for high-affinity HER2 receptor binding by an engineered protein," PNAS, 2010, 107(34):15039-15044.

Engering and Pieters, "Association of distinct tetraspanins with MHC class II molecules at different subcellular locations in human immature dendritic cells," International Immunology, 2001, 13(2):127-134.

Ferland et al., "The effect of chloroquine on lysosomal prolactin receptors in rat liver," Endocrinology, 1984, 115(5):1842-1849.

Flannery et al., "Palmitoylation-dependent association with CD63 targets the CA2+ sensor synaptotagmin VII to lysosomes," J. Cell Bioi., Nov. 2010, 191(3):599-613.

Fu et al., "Insights into HER2 signaling from step-by-step optimization of anti-HER2 antibodies," mAbs, 2014, 6(4):978-990.

Genty et al., "Endocytosis and degradation of prolactin and its receptor in Chinese hamster ovary cells stably transfected with prolactin receptor cDNA," Mol. Cell Endocrinol., 1994, 99(2):221-228.

Ghosh et al., "An Endocytosed TGN38 Chimeric Protein is Delivered to the TGN after Trafficking Through the Endocytic Recycling Comparment in CHO Cells," J. Cell Bioi., Aug. 1998, 142(4):923-936.

Gomery et al., "Antibody WN1 222-5 mimics Toll-like receptor 4 binding in the recognition of LPS," Proc. Natl. Acad. Sci USA, 2012, 109(51):20877-20882.

Gonnet et al., "Exhaustive Matching of the Entire Protein Sequence Database," Science, 1992, 256: 1443-1445.

Gordon et al., "Clinical Activity of Pertuzumab (rhuMAb 2C4), a HER Dimerization Inhibitor, in Advanced Ovarian Cancer: Potential Predictive Relationship With Tumor HER2 Activation Status," mAbs, 2006, 24(26):4324-4332.

Guan et al., "The correlation between the expression of PRL-R and ER/PR in breast cancer," Medline, 2010, 30:596-598, Accession No. 2010210497, 1 page.

Hemler et al., (2008) "Targeting of tetraspanin proteins—potential benefits and strategies," Nat. Rev. Drug. Discov. 7(9):747-758, doi:10.1038/nrd2659.

Hevir et al., "Expression of estrogen and progesterone receptors and estrogen metabolizing enzymes in different breast cancer cell lines," Chemico-Biological Interactions, 2011, 191:206-216, doi:10.1016/j.cbi.2010.12.013.

Hirst et al., "Characterization of a Fourth Adaptor-related Protein Complex," Molecular Biology of the Cell, 1999, 10:2787-2802.

Horwitz et al., "Variant T47D human breast cancer cells with high progesterone-receptor levels despite estrogen and antiestrogen resistance," Cell. Mar. 28, 1982(3):633-642.

Jackson et al., "The nuclear splicing factor RNA binding motif 5 promotes caspase activation in human neuronal cells, and increases after traumatic brain injury in mice," Journal of Cerebral Blood Flow and Metabolism: Official Journal of the International Society of Cerebral Blood Flow and Metabolism, 2015, 35(4):655-666.

Kelly et al., "Preclinical Activity of the Novel Anti-Prolactin Receptor (PRLR) Antibody-Drug Conjugate REGN2878-DM1 in PRLR-Positive Breast Cancers," Mol. Cancer Ther., 2017,16(7):1299-1311, doi:10.1158/1535-7163.MCT-16-0839.EpubApr. 4, 2017.

Klein et al., "Progress in overcoming the chain association issue in bispecific heterodimeric IgG antibodies," mAbs, 2012, 4:6 653-663 (12 pages).

Kobayashi et al., "The Tetraspanin CD63/lamp3 Cycles between Endocytic and Secretory Compartments in Human Endothelial Cells," Molecular Biology, May 2000, 11:1829-1843.

Kraft et al., "The tetraspanin CD63 is required for efficient IgE-mediated mast cell degranulation and anaphylaxis1," J. Immunol, 2013, 191(6):2871-2878.

Lambert and Chari, "Ado-trastuzumab Emtansine (T-DM1): An Antibody-Drug Conjugate (ADC) for HER2-Positive Breast Cancer," Journal of Medicinal Chemistry, (Aug. 28, 2014), 57(16):6949-6964.

Latysheva et al., "Syntenin-1 is a New Component of Tetraspanin-Enriched Microdomains: Mechanisms and Consequences of the Interaction of Syntenin-1 with CD63," Molecular and Cellular Biology, Oct. 2006, 26(20):7707-7718.

Le Doussal et al., "In Vitro and In Vivo Targeting of Radiolabeled Monovalent and Divalent Haptens with Dual Specificity Monoclonal Antibody Conjugates: Enhanced Divalent Hapten Affinity for Cell-Bound Antibody Conjugate," Journal of Nuclear Medicine, 1989, 30(8):1358.

Lee et al., "Impaired Retrograde Membrane Traffic Through Endosomes in a Mutant CHO Cell Defective in Phosphalidyl Serine Synthesis," Genes to Cells, 2012, 17:728-736.

Lee et al., "Novel strategy for a bispecific antibody: induction of dual target internalization and degradation," Oncogene, 2016, 35(34):4437-4446.

(56) References Cited

OTHER PUBLICATIONS

Lekishvili et al., "The tumour-associated antigen L6 (L6-Ag) is recruited to the tetraspanin-enriched microdomains: implication for tumour cell motility," Journal of Cell Science, 2008, 121(5):685-694, doi:10.1242/jcs.020347.
Levy and Shoham, "The Tetraspanin Web Modulates Immune-Signalling Complexes," Nat. Rev. Immunol., 2005, 5(2):136-148.
Li et al., "Cell Type and Culture Condition-Dependent Alternative Splicing in Human Breast Cancer Cells Revealed by Splicing-Sensitive Microarrays," Cancer Res., Feb. 15, 2006, 66(4):1990-1999.
Li et al., "Dkk1 Stabilizes Wnt Co-Receptor LRP6: Implication for Wnt Ligand-Induced LRP6 Down-Regulation," PLoS One Jun. 2010, 5(6):e11014.
Lieu et al., "The Golgin GCC88 is Required for Efficient Retrograde Transport of Cargo from the Early Endosomes to the Trans-Golgi Network," Mol. Bioi. Cell, Dec. 2007, 18:4979-4991.
Lloyd et al., "Modelling the human immune response: performance of a $10^{11}$ human antibody repertoire against a broad panel of therapeutically relevant antigens," Protein Engineering, Design & Selection, 2009, 22(3):159-168.
Maecker et al., "The tetraspanin superfamily: molecular facilitators," FASEB J., May 1997, 11(6)428-442.
Mantegazza et al., "CD63 Tetraspanin Slows Down Cell Migration and Translocates to the Endosomai-Lysosomal-MIICs Route after Extracellular Stimuli in Human Immature Dendritic Cells," Blood, Aug. 2004, 104(4):1183-1190.
Mabry et al., "A dual-targeting PDGFR/VEGF-A molecule assembled from stable antibody fragments demonstrates anti-angiogenic activity invitro and in vivo," mAbs, 2010, 2(1):20-34.
Martin et al., "Tetraspanins in Viral Infections: a Fundamental Role in Viral Biology?," Journal of Virology, 2005, 79(17):10839-10851.
Matsuda et al. "BRI3 inhibits amyloid precursor protein processing in a mechanistically distinct manner from its homologue dementia gene BRI2," Journal of Biological Chemistry, 2009, 284(23):15816.
Mcdonagh et al., "Antitumor Activity of a Novel Bispecific Antibody That Targets the ErbB2/ErbB3 Oncogenic Unit and Inhibits Heregulin-Induced Activation of ErbB3", Molecular Cancer Therapeutics, Mar. 2012, 11(3):582-593, XP002684950, ISSN: 1535-7163, DOI:10.1158/1535-7163.MCT-11-0820.
Metzelaar et al., "CD63 antigen. A novel lysosomal membrane glycoprotein, cloned by a screening procedure for intracellular antigens in eukaryotic cells," J. Biol. Chem., 1991, 266(5):3239-3245.
Muller-Loennies, et al., "Identification of a Cross-reactive Epitope Widely Present in Lipopolysaccharide from Enterobacteria and Recognized by the Cross-protective Monoclonal Antibody WN1 222-5," J. Biol. Chern., 2003, 278(28):25618-25627.
Nishibori et al., "The Protein CD63 is in Platelet Dense Granules, is Deficient in a Patient with Hermansky-Pudlak Syndrome, and Appears Identical to Granulophysin," J. Clin. Invest., 1993, 91(4):1775-1782.
Ollivier-Bousquet "Transferrin and Prolactin Transcytosis in the Lactating Mammary Epithelial Cell," Journal of Mammary Gland Biology and Neoplasia, 1998, 3(3):303-313.
Otto, et al., "A Neutralizing Prolactin Receptor Antibody Whose In Vivo Application Mimics the Phenotype of Female Prolactin Receptor-Deficient Mice," Endocrinology, 2015, 156: 4365-4373.
Pandey et al., "Amyloid precursor-like protein 2 (APLP2) affects the actin cytoskeleton and increases pancreatic cancer growth and metastasis," Oncotarget. Feb. 10, 2015, 6(4):2064-2075.
Pandey et al., "Amyloid precursor protein and amyloid precursor-like protein 2 in cancer," Oncotarget. Apr. 12, 2016, 7(15):19430-19444, doi:10.18632/oncotarget.7103.
Paschkowsky et al., "Alternative Processing of the Amyloid Precursor Protein Family by Rhomboid Protease RHBDL4," Journal of Biological Chemistry, 2016, 291(42): 21903-21912.
Pearson, "Using the FASTA Program to Search Protein and DNA Sequence Databases," Chapter 26, Methods Mol. Biol., 1994, 26:307-331.

Pols and Klumperman, "Trafficking and Function of the Tetraspanin CD63," Exp. Cell Res., Oct. 2009, 315:1584-1592.
Robinson et al., "Targeting ErbB2 and ErbB3 with a bispecific single-chain Fv enhances targeting selectivity and induces a therapeutic effect in vitro", British Journal of Cancer, vol. 99, No. 9, Oct. 28, 2008 (Oct. 28, 2008), pp. 1415-1425, XP009115294, ISSN: 0007-0920, DOI: 10.1038/SJ.BJC. 6604700.
Rous et al., "Role of Adaptor Complex AP-3 in Targeting Wild-Type and Mutated CD63 to Lysosomes," Molecular Biology of the Cell, Mar. 2002, 13:1071-1082.
Rubinstein et al., "CD9, CD63, CD81, and CD82 are components of a surface tetraspan network connected to HLA-DR and VLA integrins," Eur. J. Immunol., 1996, 26:2657-2665.
Schiweck et al., "Sequence analysis and bacterial production of the anti-c-myc antibody 9E10: the $V_H$ domain has an extended CDR-H3 and exhibits unusual solubility," FEBS Lett., 1997, 414(1):33-38.
Schröder et al., "Deficiency of the Tetraspanin CD63 Associated with Kidney Pathology but Normal Lysosomal Function," Mol. Cell. Biol., 2009, 29(4):1083-1094.
Scotti et al., "Additive effects of a prolactin receptor antagonist, G129R, and herceptin on inhibition of HER2-overexpressing breast cancer cells," Breast Cancer Research and Treatment, 2008, 111:241-250.
Senter, "Activation of Prodrugs by Antibody-Enzyme Conjugates: A New Approach to Cancer Therapy," FASEB J., 1990, 4:188-193.
Shahied et al., "Bispecific Minibodies Targeting HER2/neu and CD16 Exhibit Improved Tumor Lysis When Placed in a Divalent Tumor Antigen Binding Format," J. Bioi. Chern., Dec. 2004, 279(52):53907-53914.
Sharkey et al., "Bispecific Antibody Pretargeting of Radionuclides for Immuno-Single-Photon Emission Computed Tomography and Immuno-Positron Emission Tomography Molecular Imaging: An Update," Clinical Cancer Research, 2007, 13(18 Suppl):5577s-5585s.
Shen et al., "A map of the cis-regulatory sequences in the mouse genome," Nature, 2012, 488(7409):116-120, doi:10.1038/nature11243.
Takino et al., "Tetraspanin CD63 promotes targeting and lysosomal proteolysis of membrane-type 1 matrix metalloproteinase," Biochem. Biophys. Res. Commun., 2003, 304:160-166.
Tam et al., "A bispecific antibody against human IgE and human FcγRII that inhibits antigen-induced histamine release by human mast cells and basophils," Allergy, 2004, 59:772-780.
Taylor et al., "A transgenic mouse that expresses a diversity of human sequence heavy and light chain immunoglobulins," Nucl. Acids Res., 1992, 20(23):6287-6295.
Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.
Van't Veer and Van Der Poll, "Keeping blood closts at bay in sepsis," Nature Medicine, Jun. 2008, 14(6):606-608.
Yauch and Hemler, "Specific interactions among transmembrane 4 superfamily (TM4SF) proteins and phosphoinositide 4-kinase," Biochem. J., 2000, 351:629-637.
Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.
R&D Systems: "Monoclonal—Anti-human APLP-2 Antibody—Catalog No. MAB4945," R&D Systems Online Catalogue, 2019, https://resources.rndsystems.com/pdfs/datasheets/mab4945.pdf.
Atlas Antibodies: "Anti-APLP2 Product Datasheet—Product No. HPA039319," Atlas Antibodies Online Catalogue, 2019, https://atlasantibodies.com/api/print_datasheet/HPA039319.pdf.
Abcam: "Anti-APLP2 antibody ab128603," abcam Online Catalogue, https://www.abcam.com/aplp2-antibody-ab128603.pdf.
International Search Report and Written Opinion for PCT/US2016/065647, dated Jun. 8, 2017.
International Search Report and Written Opinion for PCT Application No. PCT/US2013/030636, dated Aug. 6, 2013.
International Search Report and Written Opinion for PCT Application No. PCT/US2016/041055, dated Dec. 5, 2016.

(56) References Cited

OTHER PUBLICATIONS

International Search Report and Written Opinion for PCT Application No. PCT/US2017/030250, dated Aug. 4, 2017.
Statement of Relatedness under MPEP 2001.06 with Respect to U.S. Appl. No. 16/394,849 dated Oct. 1, 2019.
Azorsa, et al. "CD63/Pltgp40: A Platelet Activation Antigen Identical to the Stage-Specific Melanoma-Associated Antigen ME491," Blood, 1991, 78(2):280-284.
Barrio, et al. "Monoclonal Antibody FC-5.01, Directed Against CD63 Antigen, is Internalized into Cytoplasmic Vesicles in the IIB-BR-G Human Breast Cancer Cell Line," Hybridoma, 1998, 17(6):517-525.
Dakour, et al. "Characterization of melanosome-associated proteins by establishment of monoclonal antibodies and immunoscreening of a melanoma cDNA library through an anti-melanosome antibody," Melanoma Research, 1993, 3(5):331-336.
Demetrick, et al. "ME491 Melanoma-Associated Glycoprotein Family: Antigenic Identity of ME491, NKI/C-3, Neuroglandular Antigen (NGA), and CD63 Proteins," Journal Natl. Cancer Inst., 1992; 84(6):422-429.
Israels and Mcmillan-Ward, "CD63 modulates spreading and tyrosine phosphorylation of platelets on immobilized fibrinogen," Thromb. Haemost., 2005, 93(2):311-318.
Kennel, et al., "Monoclonal Antibody to Rat CD63 Detects Different Molecular Form in Rat Tissue," Hybridoma, 1998, 17(6):509-515.
Kitani et al., "A Cell Surface Glycoprotein of Rat Basophilic Leukemia Cells Close to the High Affinity IgE Receptor (FcεRI)," Journal of Biological Chemistry, 1991, 266(3):1903-1909.
Knol, et al. "Monitoring human basophil activation via CD63 monoclonal antibody 435," J. Allergy Clin. Immunol., 1991, 88(3, Part 1):328-338.
Kraft et al., "Anti-CD63 antibodies suppress IgE-dependent allergic reactions in vitro and in vivo," JEM, 2005, 201(3):385-396.
Skubitz et al., "CD63 associates with tyrosine kinase activity and CD11/CD18, and transmits an activation signal in neutrophils," Journal of Immunology, 1996, 157:3617-3626.
Verjan Garcia, et al., "SIRPa/CD172a Regulates Eosinophil Homeostasis," Journal of Immunology, 2011, 187:2268-2277.
Vischer and Wagner, "CD63 is a Component of Weibel-Palade Bodies of Human Endothelial Cells," Blood, 1993, 82(4):1184-1191.
Statement of Relatedness under MPEP 2001.06 with Respect to U.S. Appl. No. 16/394,849 dated Feb. 17, 2022.
Statement of Relatedness under MPEP 2001.06 with Respect to U.S. Appl. No. 16/394,849 dated Oct. 14, 2021.
Andreev et al., "Abstract A131: Rapid constitutive internalization and degradation of prolactin receptor (PRLR) is associated with potent cell killing by PRLR antibody drug conjugates (ADC)," Molecular targets and Cancer Therapeutics, 14(12):supp. 2, Abstract No. A131 (Dec. 2015).
Audran et al., "Internalization of human macrophage surface antigens induced by monoclonal antibodies," Journal of Immunological Methods, 1995, 188:147-154.
Chen et al., "In vivo studies of the anti-tumor effects of a human prolactin antagonist, hPRL-G129R," International Journal of Oncology, 20:813-818 (2002).
Varghese et al., "Polyubiquitination of Prolactin Receptor Stimulates Its Internalization, Postinternalization Sorting, and Degradation via the Lysosomal Pathway," Molecular and Cellular Biology, 28:5275-5287 (Sep. 2008).
Life Technologies/ThermoFisher scientific product 35-9200 https://www.thermofisher.com/antibody/product/Prolactin-Receptor-Antibody-clone-1A2B1-Monoclonal/35-9200 (Accessed on Mar. 19, 2019).
Trastuzumab https://www.accessdata.fda.gov/drugsatfda_docs/label/1998/trasgen092598lb.pdf (Sep. 1998).
Dako A0485 https://www.agilent.com/cs/library/packageinsert/public/103814005.PDF (2013).
Statement of Relatedness under MPEP 2001.06 with Respect to U.S. Appl. No. 16/394,849 dated Aug. 17, 2022.

* cited by examiner

SEQUENCE LISTING

```
<160> NUMBER OF SEQ ID NOS: 4

<210> SEQ ID NO 1
<211> LENGTH: 502
<212> TYPE: PRT
<213> ORGANISM: Artificial Sequence
<220> FEATURE:
<223> OTHER INFORMATION: Synthetic

<400> SEQUENCE: 1

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190
```

```
Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
            245                 250                 255

Ser Ser Arg Leu His Thr Cys Gln Arg His Gly Pro Gly Glu Pro Arg
        260                 265                 270

Gly Pro Thr Ile Lys Pro Cys Pro Pro Cys Lys Cys Pro Ala Pro Asn
    275                 280                 285

Leu Leu Gly Gly Pro Ser Val Phe Ile Phe Pro Pro Lys Ile Lys Asp
    290                 295                 300

Val Leu Met Ile Ser Leu Ser Pro Ile Val Thr Cys Val Val Val Asp
305                 310                 315                 320

Val Ser Glu Asp Asp Pro Asp Val Gln Ile Ser Trp Phe Val Asn Asn
                325                 330                 335

Val Glu Val His Thr Ala Gln Thr Gln Thr His Arg Glu Asp Tyr Asn
            340                 345                 350

Ser Thr Leu Arg Val Val Ser Ala Leu Pro Ile Gln His Gln Asp Trp
        355                 360                 365

Met Ser Gly Lys Glu Phe Lys Cys Lys Val Asn Asn Lys Asp Leu Pro
    370                 375                 380

Ala Pro Ile Glu Arg Thr Ile Ser Lys Pro Lys Gly Ser Val Arg Ala
385                 390                 395                 400

Pro Gln Val Tyr Val Leu Pro Pro Glu Glu Glu Met Thr Lys Lys
                405                 410                 415

Gln Val Thr Leu Thr Cys Met Val Thr Asp Phe Met Pro Glu Asp Ile
            420                 425                 430

Tyr Val Glu Trp Thr Asn Asn Gly Lys Thr Glu Leu Asn Tyr Lys Asn
        435                 440                 445

Thr Glu Pro Val Leu Asp Ser Asp Gly Ser Tyr Phe Met Tyr Ser Lys
    450                 455                 460

Leu Arg Val Glu Lys Lys Asn Trp Val Glu Arg Asn Ser Tyr Ser Cys
465                 470                 475                 480

Ser Val Val His Glu Gly Leu His Asn His Thr Thr Lys Ser Phe
                485                 490                 495

Ser Arg Thr Pro Gly Lys
        500

<210> SEQ ID NO 2
<211> LENGTH: 496
<212> TYPE: PRT
<213> ORGANISM: Artificial Sequence
<220> FEATURE:
<223> OTHER INFORMATION: Synthetic

<400> SEQUENCE: 2

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45
```

```
Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
            165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
            245                 250                 255

Ser Ser Arg Leu His Thr Cys Gln Arg His Gly Pro Gly Asp Lys Thr
        260                 265                 270

His Thr Cys Pro Pro Cys Pro Ala Pro Glu Leu Leu Gly Gly Pro Ser
    275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460
```

```
Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 3
<211> LENGTH: 122
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Phe Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala His Tyr Tyr Cys
                85                  90                  95

Ala Lys Glu Ser Ser Ser Trp Tyr Phe Tyr His Gly Leu Asp Val Trp
            100                 105                 110

Gly Gln Gly Thr Met Val Thr Val Ser Ser
        115                 120

<210> SEQ ID NO 4
<211> LENGTH: 114
<212> TYPE: PRT
<213> ORGANISM: Artificial Sequence
<220> FEATURE:
<223> OTHER INFORMATION: Synthetic

<400> SEQUENCE: 4

Glu Ile Val Met Thr Gln Ser Pro Leu Ser Leu Pro Val Ser Pro Gly
1               5                   10                  15

Glu Pro Ala Ser Ile Ser Cys Arg Ser Asn Gln Ser Leu Leu His Ser
            20                  25                  30

Asn Gly Asn Asn Tyr Leu Ala Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Gly Asp Val Gly Thr Tyr Phe Cys Met Gln Ser
                85                  90                  95

Leu Gln Ala Pro Pro Phe Thr Phe Gly Pro Gly Thr Lys Val Glu Ile
            100                 105                 110

Lys Arg
```

MULTISPECIFIC ANTIGEN-BINDING MOLECULES BINDING TO A TARGET AND AN INTERNALIZING EFFECTOR PROTEIN THAT IS CD63 AND USES THEREOF

This application is a continuation of U.S. application Ser. No. 13/798,205, filed Mar. 13, 2013, which claims the benefit under 35 U.S.C. § 119(e) of U.S. provisional application No. 61/610,494, filed on Mar. 14, 2012; 61/721,831, filed on Nov. 2, 2012; and 61/751,286, filed on Jan. 11, 2013, the disclosures of which are herein incorporated by reference in their entireties.

FIELD OF THE INVENTION

The present invention relates to the field of therapeutic proteins, and in particular, to the field of therapeutic proteins that are capable of inactivating, blocking, attenuating, eliminating and/or reducing the concentration of one or more target molecules in vitro or in vivo.

BACKGROUND

Therapeutic treatments often require the inactivation or blocking of one or more target molecules that act on or in the vicinity of a cell. For example, antibody-based therapeutics often function by binding to a particular antigen expressed on the surface of a cell, or to a soluble ligand, thereby interfering with the antigen's normal biological activity. Antibodies and other binding constructs directed against various cytokines (e.g., IL-1, IL-4, IL-6, IL-13, IL-22, IL-25, IL-33, etc.), or their respective receptors, for instance, have been shown to be useful in treating a wide array of human ailments and diseases. Therapeutic agents of this type typically function by blocking the interaction between the cytokine and its receptor in order to attenuate or inhibit cellular signaling. In certain contexts, however, it would be therapeutically beneficial to inactivate or inhibit the activity of a target molecule in a manner that does not necessarily involve blocking its physical interaction with another component. One way in which such non-blocking attenuation of a target molecule could be achieved would be to reduce the extracellular or cell surface concentration of the target molecule. Although genetic and nucleic acid-based strategies for reducing the amount or concentration of a given target molecule are known in the art, such strategies are often fraught with substantial technical complications and unintended side effects in therapeutic settings. Accordingly, alternative non-blocking strategies are needed to facilitate the inactivation or attenuation of various target molecules for therapeutic purposes.

BRIEF SUMMARY OF THE INVENTION

The present invention is based, at least in part, on the concept of attenuating or inactivating a target molecule by facilitating or bringing about a physical linkage between the target molecule and an internalizing effector protein. Through this type of physical intermolecular linkage, the target molecule can be forced to be internalized into the cell along with the internalizing effector protein, and processed by the intracellular degradative machinery, or otherwise attenuated, sequestered, or inactivated. This mechanism represents a novel and inventive strategy for inactivating or attenuating the activity of a target molecule without necessarily blocking the interaction between the target molecule and its binding partners.

Accordingly, the present invention provides a multispecific antigen-binding molecule that is capable of simultaneously binding a target molecule (T) and an internalizing effector protein (E). More specifically, the present invention provides a multispecific antigen-binding molecule comprising a first antigen-binding domain (D1), and a second antigen-binding domain (D2), wherein D1 specifically binds T, and D2 specifically binds E, and wherein the simultaneous binding of T and E by the multispecific antigen-binding molecule attenuates the activity of T to a greater extent than the binding of T by D1 alone. The enhanced attenuation of the activity of T may be due to the forced internalization/degradation of T through its physical linkage to E; however, other mechanisms of action are possible and are not excluded from the scope of the present invention.

In addition, the present invention provides methods of using the multispecific antigen-binding molecule to inactivate or attenuate the activity of a target molecule (T). In particular, the present invention provides a method for inactivating or attenuating the activity of T by contacting T and an internalizing effector protein (E) with a multispecific antigen-binding molecule, wherein the multispecific antigen-binding molecule comprises a first antigen-binding domain (D1) and a second antigen-binding domain (D2), wherein D1 specifically binds T, and wherein D2 specifically binds E; and wherein the simultaneous binding of T and E by the multispecific antigen-binding molecule attenuates the activity of T to a greater extent than the binding of T by D1 alone.

In certain embodiments of the present invention, D1 and/or D2 comprise(s) at least one antibody variable region. For example, the multispecific antigen-binding molecule can, in some embodiments, be a bispecific antibody, wherein D1 comprises an antibody heavy and light chain variable region (HCVR/LCVR) pair that specifically binds T, and wherein D2 comprises an HCVR/LCVR pair that specifically binds E. Alternatively, D1 and/or D2 may comprise a peptide or polypeptide that specifically interacts with the target molecule (T) and/or the internalizing effector protein (E). For example, if the target molecule is a cell surface receptor, then D1 may comprise a portion of a ligand that specifically binds the cell surface receptor target molecule. Similarly, if the internalizing effector protein is a cell surface internalizing receptor, then D2 may comprise a portion of a ligand that specifically binds the cell surface internalizing receptor. In certain embodiments, D1 comprises an antibody variable region that specifically binds T, and D2 comprises a peptide or polypeptide that specifically binds E. In yet other embodiments, D1 comprises a peptide or polypeptide that specifically binds T, and D2 comprises an antibody variable region that specifically binds E. In any configuration, however, the end result is that T and E are capable of being physically linked, directly or indirectly, via the simultaneous binding of T and E by a multispecific antigen-binding molecule.

Other embodiments will become apparent from a review of the ensuing detailed description.

DETAILED DESCRIPTION

Figure 1:
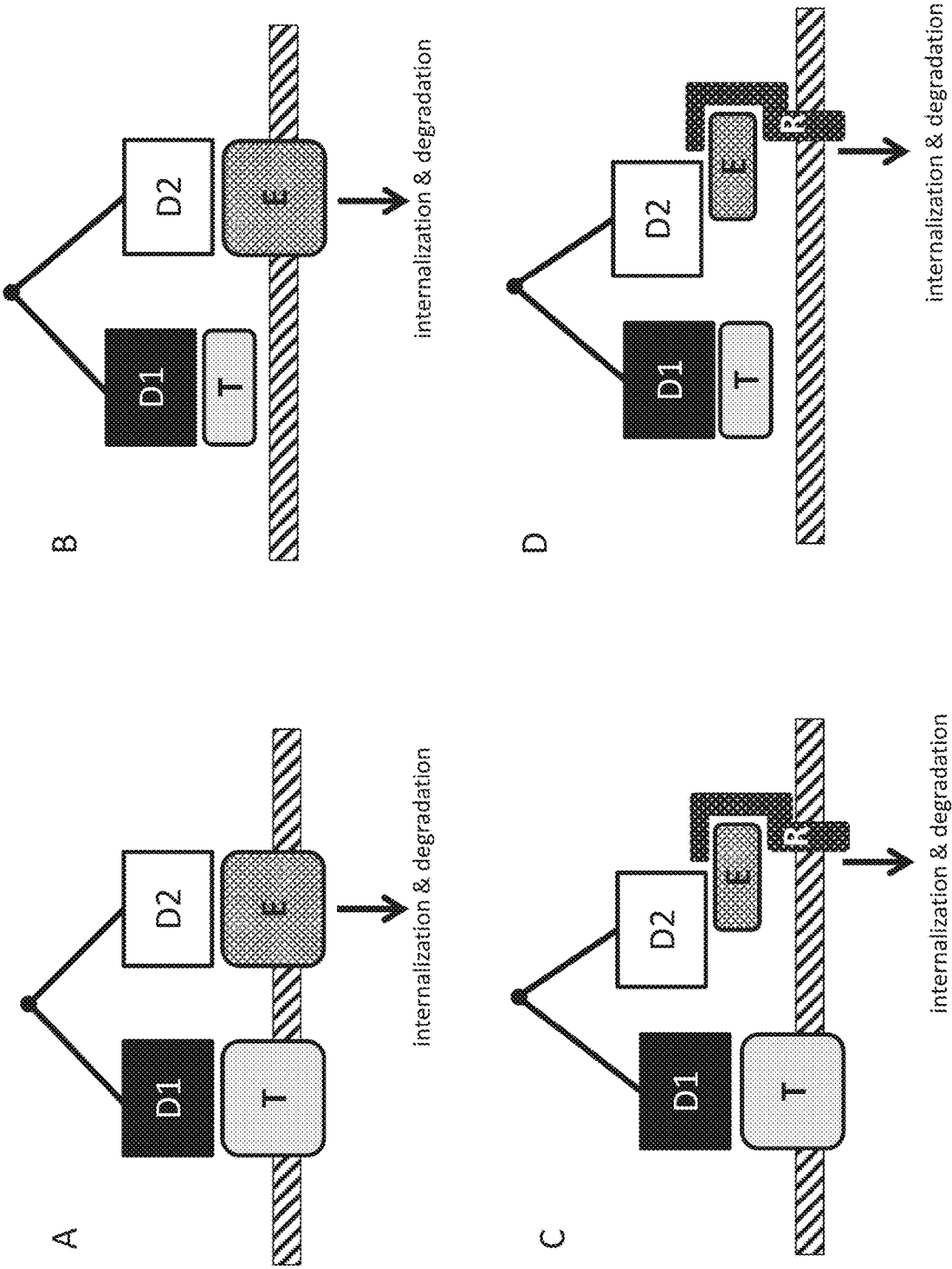
FIG. 1 (panels A-D) provides schematic representations of four general exemplary mechanisms of action for the multispecific antigen binding molecules of the present invention. In each illustrated configuration D1 is a first antigen-binding domain; D2 is a second antigen binding domain; T is a target molecule; E is an internalizing effector protein; and R is a receptor which internalizes upon binding E. Panel A depicts the situation in which both T and E are membrane-associated. Panel B depicts the situation in which T is soluble and E is membrane-associated. Panel C depicts the situation in which T is membrane-associated and E is a soluble protein that interacts with, and is internalized into the cell via the interaction of E and R. Panel D depicts the situation in which T is soluble and E is a soluble protein that interacts with, and is internalized into the cell via the interaction of E and R.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Multispecific Antigen-Binding Molecules

The present inventors have surprisingly discovered that a target molecule's activity can be attenuated by linking the target molecule to an internalizing effector protein via a multispecific antigen-binding molecule.

Accordingly, the present invention provides multispecific antigen binding molecules comprising a first antigen-binding domain (also referred to herein as "D1"), and a second antigen-binding domain (also referred to herein as "D2"). D1 and D2 each bind different molecules. D1 specifically binds a "target molecule". The target molecule is also referred to herein as "T". D2 specifically binds an "internalizing effector protein". The internalizing effector protein is also referred to herein as "E". According to the present invention, the simultaneous binding of T and E by the multispecific antigen-binding molecule attenuates the activity of T to a greater extent than the binding of T by D1 alone. As used herein, the expression "simultaneous binding," in the context of a multispecific antigen-binding molecule, means that the multispecific antigen-binding molecule is capable of contacting both a target molecule (T) and an internalizing effector protein (E) for at least some period of time under physiologically relevant conditions to facilitate the physical linkage between T and E. Binding of the multispecific antigen-binding molecule to the T and E components may be sequential; e.g., the multispecific antigen-binding molecule may first bind T and then bind E, or it may first bind E first and then bind T. In any event, so long as T and E are both bound by the multispecific antigen-binding molecule for some period of time (regardless of the sequential order of binding), the multispecific antigen-binding molecule will be deemed to "simultaneously bind" T and E for purposes of the present disclosure. Without being bound by theory, the enhanced inactivation of T is believed to be caused by the internalization and degradative rerouting of T within a cell due to its physical linkage to E. The multispecific antigen-binding molecules of the present invention are thus useful for inactivating and/or reducing the activity and/or extracellular concentration of a target molecule without directly blocking or antagonizing the function of the target molecule.

According to the present invention, a multispecific antigen-binding molecule can be a single multifunctional polypeptide, or it can be a multimeric complex of two or more polypeptides that are covalently or non-covalently associated with one another. As will be made evident by the present disclosure, any antigen binding construct which has the ability to simultaneously bind a T and an E molecule is regarded as a multispecific antigen-binding molecule. Any of the multispecific antigen-binding molecules of the invention, or variants thereof, may be constructed using standard molecular biological techniques (e.g., recombinant DNA and protein expression technology), as will be known to a person of ordinary skill in the art.

Antigen-Binding Domains

The multispecific antigen-binding molecules of the present invention comprise at least two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest. The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

In certain embodiments in which the target molecule or the internalizing effector protein is a receptor molecule, an "antigen-binding domain," for purposes of the present invention, may comprise or consist of a ligand or portion of a ligand that is specific for the receptor. For example, if the target molecule (T) is IL-4R, the D1 component of the multispecific antigen-binding molecule may comprise the IL-4 ligand or a portion of the IL-4 ligand that is capable of specifically interacting with IL-4R; or if the internalizing effector protein (E) is transferrin receptor, the D2 component of the multispecific antigen-binding molecule may comprise transferrin or a portion of transferrin that is capable of specifically interacting with the transferrin receptor.

In certain embodiments in which the target molecule or the internalizing effector protein is a ligand that is specifically recognized by a particular receptor (e.g., a soluble target molecule), an "antigen-binding domain," for purposes of the present invention, may comprise or consist of the receptor or a ligand-binding portion of the receptor. For example, if the target molecule (T) is IL-6, the D1 component of the multispecific antigen-binding molecule may comprise the ligand-binding domain of the IL-6 receptor; or if the internalizing effector protein (E) is an indirectly internalized protein (as that term is defined elsewhere herein), the D2 component of the multispecific antigen-binding molecule may comprise a ligand-binding domain of a receptor specific for E.

Methods for determining whether two molecules specifically bind one another are well known in the art and include, for example, equilibrium dialysis, surface plasmon resonance, and the like. For example, an antigen-binding domain, as used in the context of the present invention, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies and Antigen-Binding Fragments of Antibodies

As indicated above, an "antigen-binding domain" (D1 and/or D2) can comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., T or E). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain (CO). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The D1 and/or D2 components of the multispecific antigen-binding molecules of the present invention may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The multispecific antigen-binding molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The multispecific antigen-binding molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Bispecific Antibodies

According to certain embodiments, the multispecific antigen-binding molecules of the invention are bispecific antibodies; e.g., bispecific antibodies comprising an antigen-binding arm that specifically binds a target molecule (T) and an antigen-binding arm that specifically binds an internalizing effector protein (E). Methods for making bispecific antibodies are known in the art and may be used to construct multispecific antigen-binding molecules of the present invention. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

Multimerizing Components

The multispecific antigen-binding molecules of the present invention, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the multispecific antigen-binding molecules of the present invention comprise two multimerizing domains, M1 and M2, wherein D1 is attached to M1 and D2 is attached to M2, and wherein the association of M1 with M2 facilitates the physical linkage of D1 and D2 to one another in a single multispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

Internalizing Effector Proteins (E)

In the context of the present invention, the D2 component of the multispecific antigen-binding molecule specifically binds an internalizing effector protein ("E"). An internalizing effector protein is a protein that is capable of being internalized into a cell or that otherwise participates in or contributes to retrograde membrane trafficking. In some instances, the internalizing effector protein is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of D2 to an internalizing effector protein causes the entire multispecific antigen-binding molecule, and any molecules associated therewith (e.g., a target molecule bound by D1), to also become internalized into the cell. As explained below, internalizing effector proteins include proteins that are directly internalized into a cell, as well as proteins that are indirectly internalized into a cell.

Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway. Specific non-limiting examples of internalizing effector proteins that are directly internalized into a cell include, e.g., CD63, MHC-I (e.g., HLA-B27), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (Myelin And Lymphocyte protein, a.k.a. VIP17), IGF2R, vacuolar-type $H^+$ ATPase, diphtheria toxin receptor, folate receptor, glutamate receptors, glutathione receptor, leptin receptors, scavenger receptors (e.g., SCARA1-5, SCARB1-3, CD36), etc.

In embodiments in which E is a directly internalized effector protein, the D2 component of the multispecific antigen-binding molecule can be, e.g., an antibody or antigen-binding fragment of an antibody that specifically binds E, or a ligand or portion of a ligand that specifically interacts with the effector protein. For example, if E is Kremen-1 or Kremen-2, the D2 component can comprise or consist of a Kremen ligand (e.g., DKK1) or Kremen-binding portion thereof. As another example, if E is a receptor molecule such as ASGR1, the D2 component can comprise or consist of a ligand specific for the receptor (e.g., asialoorosomucoid [ASOR] or Beta-GalNAc) or a receptor-binding portion thereof.

Internalizing effector proteins that are indirectly internalized into a cell include proteins and polypeptides that do not internalize on their own, but become internalized into a cell after binding to or otherwise associating with a second protein or polypeptide that is directly internalized into the cell. Proteins that are indirectly internalized into a cell include, e.g., soluble ligands that are capable of binding to an internalizing cell surface-expressed receptor molecule. A non-limiting example of a soluble ligand that is (indirectly) internalized into a cell via its interaction with an internalizing cell surface-expressed receptor molecule is transferrin. In embodiments wherein E is transferrin (or another indirectly internalized protein), the binding of D2 to E, and the interaction of E with transferrin receptor (or another internalizing cell-surface expressed receptor molecule), causes the entire multispecific antigen-binding molecule, and any molecules associated therewith (e.g., a target molecule bound by D1), to become internalized into the cell concurrent with the internalization of E and its binding partner.

In embodiments in which E is an indirectly internalized effector protein such as a soluble ligand, the D2 component of the multispecific antigen-binding molecule can be, e.g., an antibody or antigen-binding fragment of an antibody that specifically binds E, or a receptor or portion of a receptor that specifically interacts with the soluble effector protein. For example, if E is a cytokine, the D2 component can comprise or consist of the corresponding cytokine receptor or ligand-binding portion thereof.

Target Molecules (T)

In the context of the present invention, the D1 component of the multispecific antigen-binding molecule specifically binds a target molecule ("T"). A target molecule is any protein, polypeptide, or other macromolecule whose activity or extracellular concentration is desired to be attenuated, reduced or eliminated. In many instances, the target molecule to which D1 binds is a protein or polypeptide [i.e., a "target protein"]; however, the present invention also includes embodiments wherein the target molecule ("T") is a carbohydrate, glycoprotein, lipid, lipoprotein, lipopolysaccharide, or other non-protein polymer or molecule to which D1 binds. According to the present invention, T can be a cell surface-expressed target protein or a soluble target protein. Target binding by the multispecific antigen-binding molecule may take place in an extracellular or cell surface context. In certain embodiments, however, the multispecific antigen-binding molecule binds a target molecule inside the cell, for example within an intracellular component such as the endoplasmic reticulum, Golgi, endosome, lysosome, etc.

Examples of cell surface-expressed target molecules include cell surface-expressed receptors, membrane-bound ligands, ion channels, and any other monomeric or multimeric polypeptide component with an extracellular portion that is attached to or associated with a cell membrane. Non-limiting, exemplary cell surface-expressed target molecules that may be targeted by the multispecific antigen-binding molecule of the present invention include, e.g., cytokine receptors (e.g., receptors for IL-1, IL-4, IL-6, IL-13, IL-22, IL-25, IL-33, etc.), as well as cell surface targets including other type 1 transmembrane receptors such as PRLR, G-protein coupled receptors such as GCGR, ion channels such as Nav1.7, ASIC1 or ASIC2, non-receptor surface proteins such as MHC-I (e.g., HLA-B*27), etc.

In embodiments in which T is a cell surface-expressed target protein, the D1 component of the multispecific antigen-binding molecule can be, e.g., an antibody or antigen-binding fragment of an antibody that specifically binds T, or a ligand or portion of a ligand that specifically interacts with the cell surface-expressed target protein. For example, if T is IL-4R, the D1 component can comprise or consist of IL-4 or a receptor-binding portion thereof.

Examples of soluble target molecules include cytokines, growth factors, and other ligands and signaling proteins. Non-limiting exemplary soluble target protein that may be targeted by the multispecific antigen-binding molecule of the present invention include, e.g., IL-1, IL-4, IL-6, IL-13, IL-22, IL-25, IL-33, SOST, DKK1, etc. Soluble targets molecules also include, e.g., non-human target molecules such as allergens (e.g., Fel D1, Betv1, CryJ1), pathogens (e.g., *Candida albicans, S. aureus*, etc.), and pathogenic molecules (e.g., lipopolysaccharide [LPS], lipotechoic acid [LTA], Protein A., toxins, etc.). In embodiments in which T is a soluble target molecule, the D1 component of the multispecific antigen-binding molecule can be, e.g., an antibody or antigen-binding fragment of an antibody that specifically binds T, or a receptor or portion of a receptor that specifically interacts with the soluble target molecule. For example, if T is IL-4, the D1 component can comprise or consist of IL-4R or a ligand-binding portion thereof.

Target molecules also include tumor-associated antigens, as described elsewhere herein.

pH-Dependent Binding

The present invention provides multispecific antigen-binding molecules comprising a first antigen-binding domain (D1) and a second antigen-binding domain (D2), wherein one or both of the antigen-binding domains (D1 and/or D2) binds its antigen (T or E) in a pH-dependent manner. For example, an antigen-binding domain (D1 and/or D2) may exhibit reduced binding to its antigen at acidic pH as compared to neutral pH. Alternatively, an antigen-binding domain (D1 and/or D2) may exhibit enhanced binding to its antigen at acidic pH as compared to neutral pH. Antigen-binding domains with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antigen-binding domains with pH-dependent characteristics. For example, by substituting one or more amino acid of an antigen-binding domain (e.g., within a CDR) with a histidine residue, an antigen-binding domain with reduced antigen-binding at acidic pH relative to neutral pH may be obtained.

In certain embodiments, the present invention includes multispecific antigen-binding molecules comprising a D1 and/or D2 component that binds its respective antigen (T or E) at acidic pH with a $K_D$ that is at least about 3, 5, 10, 11, 12, 13, 14, 15, 16, 17, 18, 19, 20, 25, 30, 35, 40, 45, 50, 55, 60, 65, 70, 75, 80, 85, 90, 95, 100, or more times greater than the $K_D$ of the D1 and/or D2 component for binding to its respective antigen at neutral pH. pH dependent binding may also be expressed in terms of the t½ of the antigen-binding domain for its antigen at acidic pH compared to neutral pH. For example, the present invention includes multispecific antigen-binding molecules comprising a D1 and/or D2 component that binds its respective antigen (T or E) at acidic pH with a t½ that is at least about 5, 6, 7, 8, 9, 10, 15, 20, 25, 30, 35, 40, 45, 50, 55, 60, or more times shorter than the t½ of the D1 and/or D2 component for binding to its respective antigen at neutral pH.

Multispecific antigen-binding molecules of the present invention that comprise a D1 and/or D2 component with reduced antigen binding at acidic pH as compared to neutral pH, when administered to animal subjects, may in certain embodiments exhibit slower clearance from circulation as compared to comparable molecules that do not exhibit pH-dependent binding characteristics. According to this aspect of the invention, multispecific antigen-binding molecules with reduced antigen binding to either T and/or E at acidic pH as compared to neutral pH are provided which exhibit at least 2 times slower clearance from circulation relative to comparable antigen-binding molecules that do not possess reduced antigen binding at acidic pH as compared to neutral pH. Clearance rate can be expressed in terms of the half-life of the antibody, wherein a slower clearance correlates with a longer half-life.

As used herein, the expression "acidic pH" means a pH of 6.0 or less. The expression "acidic pH" includes pH values of about 6.0, 5.95, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Attenuation of Target Molecule Activity

As noted elsewhere herein, and as demonstrated by the working Examples herein below, the present inventors have discovered that the simultaneous binding of a target molecule (T) and an internalizing effector protein (E) by a multispecific antigen-binding molecule attenuates the activity of T to a greater extent than the binding of T by the first antigen-binding domain (D1) component of the multispecific antigen-binding molecule alone. As used herein, the expression "attenuates the activity of T to a greater extent than the binding of T by D1 alone" means that, in an assay in which the activity of T can be measured using cells that express E, the level of T activity measured in the presence of a multispecific antigen-binding molecule is at least 10% lower than the level of T activity measured in the presence of a control construct containing D1 by itself (i.e., not physically linked to the second antigen-binding domain (D2)). For instance, the level of T activity measured in the presence of the multispecific antigen-binding molecule may be about 10%, 15%, 20%, 25%, 30%, 35%, 40%, 45%, 50%, 55%, 60%, 65%, 70%, 75%, 80%, 85%, 90%, 95%, or 100% lower than the level of T activity measured in the presence of a control construct containing D1 by itself.

A non-limiting, illustrative assay format for determining whether a multispecific antigen-binding molecule attenuates the activity of a target molecule to a greater extent than the binding of the target molecule by the D1 domain alone is shown in working Examples 1 and 2, herein below. In Example 1, for instance, "T" is the interleukin-4 receptor (IL-4R), and "E" is CD63. The multispecific antigen-binding molecule of Example 1 is a 2-antibody conjugate comprising an anti-IL-4R mAb linked to an anti-CD63 mAb via a streptavidin/biotin linker. Thus, "D1" in this exemplary construct is the antigen-binding domain (HCVR/LCVR pair) of the anti-IL-4R antibody, and "D2" is the antigen-binding domain (HCVR/LCVR pair) of the anti-CD63 antibody. For the experiments of Examples 1 and 2, a cell-based assay format was used that produces a reporter signal when IL-4R activity is stimulated by the addition of exogenous IL-4 ligand. The amount of IL-4-induced reporter activity detected in the presence of the multispecific antigen-binding molecule was compared to the amount of IL-4-induced reporter activity detected in the presence of control constructs containing the anti-IL-4R antibody either connected to an irrelevant control immunoglobulin (control 1), or combined with, but not physically connected to, the anti-CD63 antibody (control 2). The control constructs thus produce the condition in which T is bound by D1 alone (i.e., wherein D1 is not a part of the multispecific antigen-binding molecule per se). If the extent of target molecule activity (represented by the reporter signal) observed in the presence of the multispecific antigen-binding molecule is at least 10% less than the amount of target molecule activity observed in the presence of a control construct comprising the D1 component not physically linked to the D2 component (e.g., control 1 or control 2), then for purposes of the present disclosure, it is concluded that "the simultaneous binding of T and E by the multispecific antigen-binding molecule attenuates the activity of T to a greater extent than the binding of T by D1 alone."

The binding of T by D1 alone may, in some embodiments, result in partial attenuation of the activity of T (as in the case of Example 2 where the treatment of reporter cells with an anti-IL-4R antibody alone [i.e., controls 1 and 2] caused a small level of attenuation of IL-4 signaling relative to untreated cells). In other embodiments, the binding of T by D1 alone will result in no detectable attenuation of the activity of T; that is, the biological activity of T may be unaffected by the binding of T by D1 alone. In any event, however, the simultaneous binding of T and E by a multispecific antigen-binding molecule of the invention will attenuate the activity of T to a greater extent than the binding of T by D1 alone.

Alternative assay formats and variations on the assay format(s) exemplified herein will be apparent to persons of ordinary skill in the art, taking into account the nature of the specific target molecule and effector proteins to which any given multispecific antigen-binding molecule may be directed. Any such format can be used in the context of the present invention to determine whether the simultaneous binding of T and E by a multispecific antigen-binding molecule attenuates the activity of T to a greater extent than the binding of T by D1 alone.

Tumor Targeting

In another aspect of the invention, the multispecific antigen-binding molecules are useful for targeting tumor cells. According to this aspect of the invention, the target molecule "T" to which D1 binds is a tumor-associated antigen. In certain instances, the tumor-associated antigen is an antigen that is not ordinarily internalized. The internalizing effector protein "E" to which D2 binds may be tumor specific, or it may be expressed on both tumor and non-tumor cells of an individual. Any of the internalizing effector proteins mentioned elsewhere herein may be targeted for anti-tumor applications of the invention.

As used herein, the term "tumor-associated antigen" includes proteins or polypeptides that are preferentially expressed on the surface of a tumor cell. The expression "preferentially expressed," as used in this context, means that the antigen is expressed on a tumor cell at a level that is at least 10% greater (e.g., 10%, 20%, 30%, 40%, 50%, 60%, 70%, 80%, 90%, 100%, 110%, 150%, 200%, 400%, or more) than the expression level of the antigen on non-tumor cells. In certain embodiments, the target molecule is an antigen that is preferentially expressed on the surface of a tumor cell selected from the group consisting of a renal tumor cell, a colon tumor cell, a breast tumor cell, an ovarian tumor cell, a skin tumor cell, a lung tumor cell, a prostate tumor cell, a pancreatic tumor cell, a glioblastoma cell, a head and neck tumor cell and a melanoma cell. Non-limiting examples of specific tumor-associated antigens include, e.g., AFP, ALK, BAGE proteins, β-catenin, brc-abl, BRCA1, BORIS, CA9, carbonic anhydrase IX, caspase-8, CD40, CDK4, CEA, CTLA4, cyclin-B1, CYP1B1, EGFR, EGFRvIII, ErbB2/Her2, ErbB3, ErbB4, ETV6-AML, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

The multispecific antigen-binding molecule, according to this aspect of the invention, may be conjugated to a drug, toxin, radioisotope, or other substance which is detrimental to the viability of a cell. Alternatively, the drug or toxin may be a substance which does not directly kill a cell, but renders a cell more susceptible to killing by other external agents. In yet other embodiments involving tumor targeting, the multispecific antigen-binding molecule of the invention is not itself conjugated to a drug, toxin or radioisotope, but instead is administered in combination with a second antigen-binding molecule specific for the target (T) (herein referred to as an "accomplice molecule"), wherein the accomplice molecule is conjugated to a drug, toxin or radioisotope. In such embodiments, the multispecific antigen binding molecule will preferably bind to an epitope on the target molecule (T) that is distinct from and/or non-overlapping with the epitope recognized by the accomplice molecule (i.e., to allow for simultaneous binding of the multispecific antigen-binding molecule and the accomplice molecule to the target).

In a related embodiment, the present invention also includes anti-tumor combinations, and therapeutic methods, comprising: (a) a toxin- or drug-conjugated antigen-binding molecule that specifically binds a tumor-associated antigen; and (b) a multispecific antigen-binding molecule comprising (i) a first binding domain that specifically binds an internalizing effector protein (e.g., with low affinity) and (ii) a second binding domain that specifically binds the toxin- or drug-conjugated antigen-binding molecule. In this embodiment, the multispecific antigen-binding molecule functions to link the toxin- or drug-conjugated antigen-binding molecule to the internalizing effector protein, which thereby functions to physically link the tumor associated antigen to the internalizing effector protein. Internalization of the toxin-labeled anti-tumor-associated antigen antibody via its connection to the internalizing effector protein would consequently result in targeted tumor cell killing.

According to certain embodiments of the tumor-targeting aspects of the invention, the multispecific antigen-binding molecule (or accomplice antibody) may be conjugated to one or more cytotoxic drugs selected from the group consisting of: calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, larotaxel, tesetaxel, orataxel, docetaxel, dolastatin 10, auristatin E, auristatin PHE and maytansine-based compounds (e.g., DM1, DM4, etc.). The multispecific antigen-binding molecule (or accomplice antibody) may also, or alternatively, be conjugated to a toxin such as diphtheria toxin, Pseudomonas aeruginosa exotoxin A, ricin A chain, abrin A chain, modeccin A chain, alpha-sarcin, Aleurites fordii proteins, dianthin proteins, Phytolaca americana proteins, etc. The multispecific antigen-binding molecule (or accomplice antibody) may also, or alternatively, be conjugated to one or more radioisotope selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{121}$Pb, $^{224}$Ra and $^{223}$Ra. Thus, this aspect of the invention includes multispecific antigen-binding molecules that are antibody-drug conjugates (ADCs) or antibody-radioisotope conjugates (ARCs).

In the context of tumor killing applications, the D2 component may, in certain circumstances, bind with low affinity to the internalizing effector protein "E". Thus, the multispecific antigen-binding molecule will preferentially target tumor cells that express the tumor-associated antigen. As used herein, "low affinity" binding means that the binding affinity of the D2 component for the internalizing effector protein (E) is at least 10% weaker (e.g., 15% weaker, 25% weaker, 50% weaker, 75% weaker, 90% weaker, etc.) than the binding affinity of the D1 component for the target molecule (T). In certain embodiments, "low affinity" binding means that the D2 component interacts with the internalizing effector protein (E) with a $K_D$ of greater than about 10 nM to about 1 pM, as measured in a surface plasmon resonance assay at about 25° C.

The simultaneous binding of a multispecific antigen-binding molecule to an internalizing effector protein and a tumor-associated antigen will result in preferential internalization of the multispecific antigen-binding molecule into tumor cells. If, for example, the multispecific antigen-binding molecule is conjugated to a drug, toxin or radioisotope (or if the multispecific antigen-binding molecule is administered in combination with an accomplice antibody that is conjugated to a drug, toxin or radioisotope), the targeted internalization of the tumor-associated antigen into the tumor cell via its linkage to the multispecific antigen-binding molecule, will result in extremely specific tumor cell killing.

Pharmaceutical Compositions and Administration Methods

The present invention includes pharmaceutical compositions comprising a multispecific antigen-binding molecule. The pharmaceutical compositions of the invention can be formulated with suitable carriers, excipients, and other agents that provide improved transfer, delivery, tolerance, and the like.

The present invention also includes methods for inactivating or attenuating the activity of a target molecule (T). The methods of the present invention comprise contacting a target molecule with a multispecific antigen-binding molecule as described herein. In certain embodiments, the methods according to this aspect of the invention comprise administering a pharmaceutical composition comprising a multispecific antigen-binding molecule to a patient for whom it is desirable and/or beneficial to inactivate, attenuate, or otherwise decrease the extracellular concentration of a target molecule.

Various delivery systems are known in the art and can be used to administer the pharmaceutical compositions of the present invention to a patient. Methods of administration that can be used in the context of the present invention include, but are not limited to, intradermal, intramuscular, intraperitoneal, intravenous, subcutaneous, intranasal, epidural, and oral routes. The pharmaceutical compositions of the invention may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. For example, a pharmaceutical composition of the present invention can be delivered subcutaneously or intravenously with a standard needle and syringe. In addition, with respect to subcutaneous delivery, a pen delivery device can be used to administer a pharmaceutical composition of the present invention to a patient.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Use of a Multispecific Antigen-Binding Molecule to Induce Degradation of a Cell Surface Receptor Via Linkage with an Internalizing Effector Protein As an initial proof-of-concept experiment, a multispecific antigen-binding molecule was created which is capable of binding (a) an internalizing effector molecule and (b) a cell surface receptor target molecule. In this Example, the internalizing effector protein is Kremen-2 (Krm2), and the cell surface receptor target molecule is an Fc receptor (FcγR1 [Fc-gamma-R1]).

Kremen molecules (Krm1 and Krm2) are cell-surface proteins known to mediate WNT signaling by directing the internalization and degradation of the WNT pathway signaling molecules LRP5 and LRP6. Internalization of LRP5/6 is accomplished via the soluble interacting protein DKK1. In particular, DKK1 links Kremen to LRP5/6 on the cell surface, and because of this linkage, the internalization of Kremen drives the internalization and degradation of LRP5 and LRP6. (See Li et al., PLoS One 5(6):e11014).

The present inventors sought to exploit the Kremen-binding properties of DKK1 and the internalization properties of Kremen to induce the internalization of FcγR1. To facilitate Kremen-mediated internalization/degradation of FcγR1, a multispecific antigen-binding molecule was constructed consisting of DKK1 fused to a mouse Fc (DKK1-mFc, having the amino acid sequence of SEQ ID NO:1). As explained elsewhere herein, a multispecific antigen-binding molecule is defined as a molecule comprising a first antigen-binding domain (D1) which specifically binds a target molecule, and a second antigen-binding domain (D2) which specifically binds an internalizing effector protein. In this proof-of-concept Example, the "first antigen-binding domain" is the mFc component which specifically binds the target molecule FcγR1, and the "second antigen-binding domain" is the DKK1 component which specifically binds the internalizing effector protein Kremen.

An experiment was first conducted to determine whether DKK1-mFc can be endocytosed into cells in a Kremen-dependent manner. For this experiment, two cell lines were used: Cell-1, an HEK293 cell line engineered to express FcγR1 but not Kremen-2, and Cell-2, an HEK293 cell line engineered to express both FcγR1 and Kremen-2. A 1:10 dilution of DKK1-mFc conditioned medium was added to the respective cell lines and allowed to incubate at 37° C. for 90 minutes. After the 90 minute incubation, cells were stained with Alexa-488-labeled anti-mouse IgG antibody to detect the DKK1-mFc molecule. Using fluorescence microscopy, it was observed that virtually no DKK1-mFc was localized inside Cell-1 (lacking Kremen); however, substantial amounts of DKK1-mFc were detected within Cell-2 which expresses Kremen-2. Thus, these results show that the multispecific antigen-binding molecule DKK1-mFc can be internalized into cells in a Kremen-dependent manner.

Next, a time-course experiment was conducted to determine whether DKK1-mFc can induce FcγR1 degradation in a Kremen-dependent manner. A brief description of the experimental protocol is as follows: Cell-1 (expressing only FcγR1) and Cell-2 (expressing Kremen-2 and FcγR1) were treated with 2 mg/ml NHS-Sulfo-Biotin for 15 minutes on ice to label all cell surface expressed proteins. Cells were then washed and resuspended in 400 µl of medium and divided into four-100 µl aliquots which were treated with DKK1-mFc for varying amounts of time (0 min, 15 min, 30 min and 60 min) at 37° C. Following DKK1-mFc incubation, cells were pelleted and treated with protease inhibitors. Lysates of the cells from the different incubation time points were subjected to FcγR1 immunoprecipitation. For the FcγR1 immunoprecipitation, mouse anti-FcγR1 antibody was added to cell lysates and incubated for 1 hour at 4° C. Then Protein-G beads were added and the mixture was incubated for 1 hour at 4° C. The beads were then washed and the proteins eluted and subjected to SDS-PAGE. Proteins were transferred to membrane and probed with HRP-labeled streptavidin to reveal relative amounts of remaining surface-exposed FcγR1 protein in each sample. Results are shown in FIG. 2.

Figure 2:
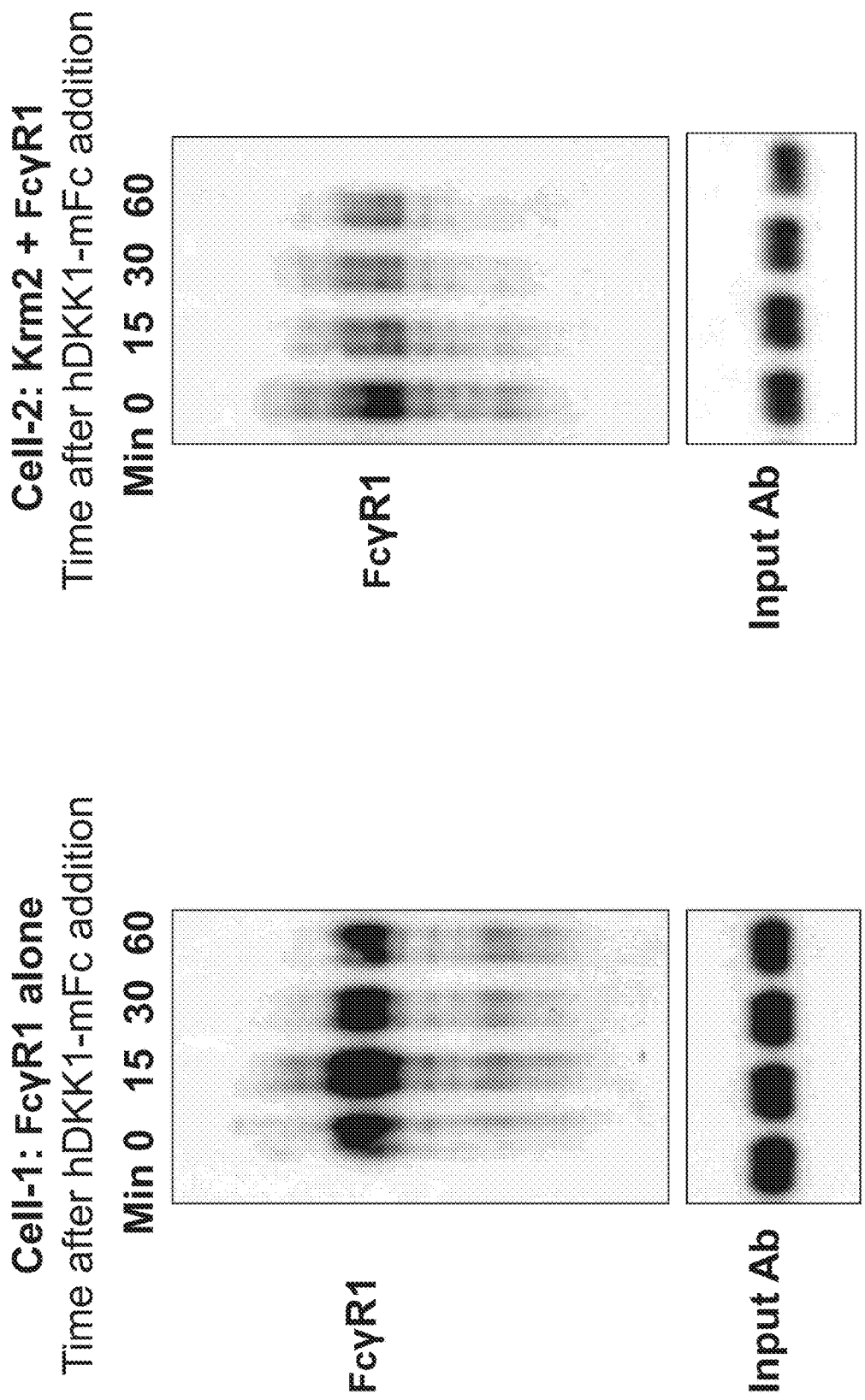
FIG. 2 shows the results of an immunoprecipitation experiment performed on two different cells (Cell-1 expressing FcγR1 alone, and Cell-2 expressing Krm2 and FcγR1) following incubation for different amounts of time (0, 15, 30 and 60 minutes) with a DKK1-mFc multispecific antigen-binding molecule.

As illustrated in FIG. 2, the amount of surface-exposed FcγR1 protein in Cell-1 samples (expressing FcγR1 but not Kremen-2) remained relatively constant regardless of the amount of time the cells were exposed to DKK1-mFc. By contrast, the amount of surface-exposed FcγR1 protein in Cell-2 samples (expressing both Kremen-2 and FcγR1) decreased substantially with increasing incubation times with DKK1-mFc. Thus, this experiment demonstrates that DKK1-mFc induces degradation of cell surface expressed FcγR1 in a Kremen-2-dependent manner.

Taken together, the foregoing results show that a multispecific antigen-binding molecule that simultaneously binds a cell surface target molecule (FcγR1) and an internalizing effector protein (Kremen-2), can induce degradation of the target molecule in an effector protein-dependent manner.

Example 2

IL-4R Activity is Attenuated Using a Multispecific Antigen-Binding Molecule with Specificity for IL-4R and CD63

In a further set of proof-of-concept experiments, a multispecific antigen-binding molecule was constructed which is capable of simultaneously binding a cell surface-expressed target molecule (i.e., IL-4R) and a cell surface-expressed internalizing effector protein (i.e., CD63). The purpose of these experiments was to determine whether IL-4R activity on a cell can be attenuated to a greater extent by physically linking IL-4R to an effector molecule that is internalized and targeted for degradation within the lysosome (in this case, CD63). In other words, this Example was designed to test whether the normal internalization and degradation of CD63 could be used to force the internalization and degradative rerouting of IL-4R within a cell.

First, a multispecific antigen-binding molecule was constructed that is able to bind both IL-4R and CD63. Specifically, a streptavidin-conjugated anti-IL-4R antibody and a biotinylated anti-CD63 antibody were combined in a 1:1 ratio to produce an anti-IL-4R:anti-CD63 conjugate (i.e., a multispecific antigen-binding molecule that specifically binds both IL-4R and CD63). The anti-IL-4R antibody used in this Example is a fully human mAb raised against the IL-4R extracellular domain. (The anti-IL-4R antibody comprised a heavy chain variable region having SEQ ID NO:3 and a light chain variable region having SEQ ID NO:4). The anti-CD63 antibody used in this Example is the mouse anti-human CD63 mAb clone MEM-259, obtained from Biolegend (San Diego, Calif.), catalog. No. 312002.

Two control constructs were also created: Control-1=streptavidin-conjugated anti-IL-4R antibody combined in a 1:1 ratio with biotinylated control mouse IgG1kappa antibody; and Control-2=streptavidin-conjugated anti-IL-4R antibody combined in a 1:1 ratio with non-biotinylated anti-CD63 antibody. The anti-IL-4R antibody used in the experimental and control constructs for this Example is an antibody that is known to specifically bind IL-4R and only partially block IL-4-mediated signaling.

The experimental cell line used in this Example is an HEK293 cell line containing a STAT6-luciferase reporter construct and additional STAT6 ("HEK293/STAT6-luc cells"). The cells used in this experiment express both IL-4R and CD63 on their surface. When treated with IL-4 in the absence of any inhibitors, this cell line produces a dose-dependent detectable chemiluminescence signal which reflects the extent of IL-4-mediated signaling.

Figure 3:
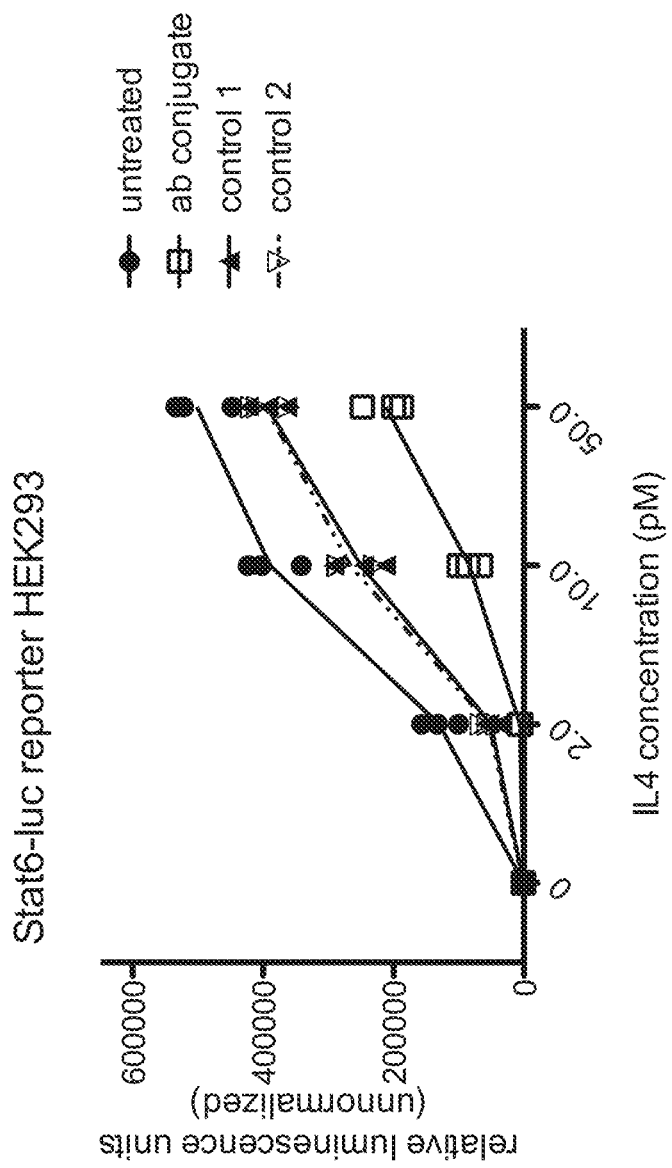
FIG. 3 shows the relative IL-4-induced luminescence produced by Stat6-luc reporter HEK293 cells in the presence and absence of an anti-IL-4R/anti-CD63 multispecific antigen binding protein ("ab conjugate") or control constructs ("control 1" and "control 2") at various concentrations of IL-4.

In an initial experiment, the experimental anti-IL-4R/anti-CD63 multispecific molecule, or the control constructs, were added to the HEK293/STAT6-luc cells so that the final concentration of anti-IL-4R antibody in the media was 12.5 nM. Reporter signal was measured at increasing concentrations of IL-4 in the presence and absence of the experimental and control constructs (FIG. 3). As seen in FIG. 3, The anti-IL-4R/anti-CD63 multispecific molecule ("ab conjugate") inhibited IL-4-mediated signaling to a significantly greater extent than either control construct.

Figure 4:
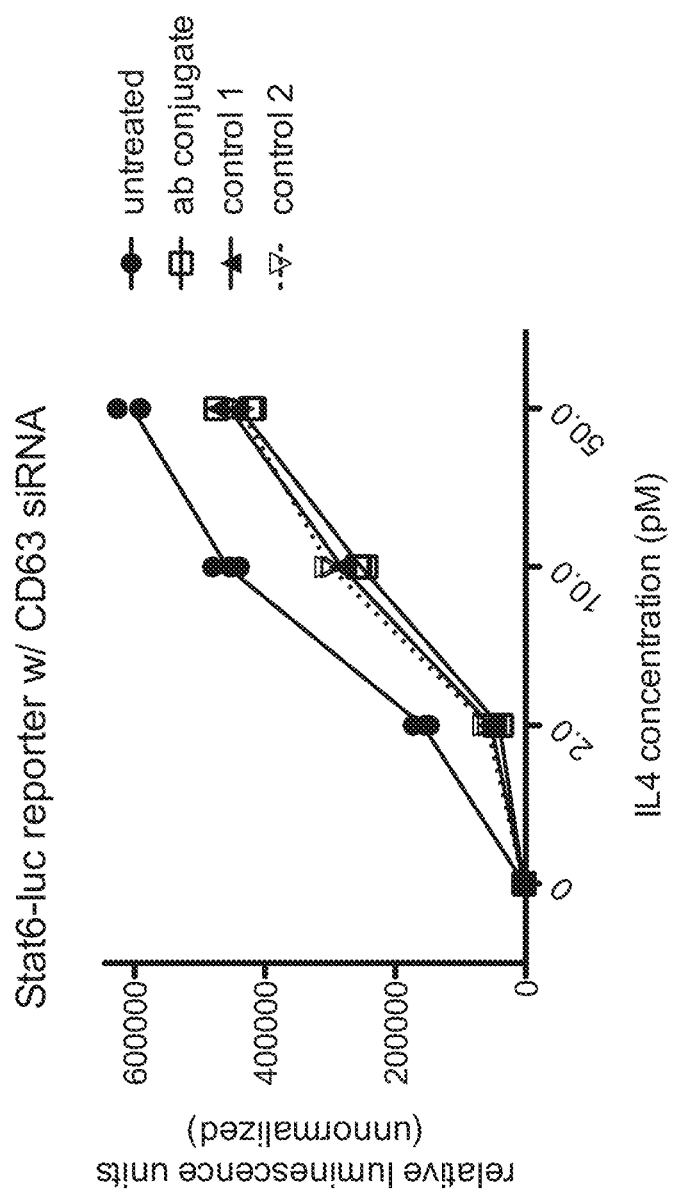
FIG. 4 shows the results of an experiment carried out in the same manner as the experiment shown in FIG. 3, except that CD63 expression was significantly reduced in the reporter cell line by an siRNA directed against CD63.

To confirm that the effect observed in FIG. 3 was dependent on CD63, the same experiment described above was carried out, except that CD63 expression was significantly reduced in the reporter cell line using an siRNA directed against CD63. With CD63 expression significantly reduced, the enhanced inhibitory activity of the anti-IL-4R/anti-CD63 multispecific molecule was no longer observed (FIG. 4). This result suggests that the ability of the anti-IL-4R/anti-CD63 multispecific molecule to attenuate IL-4-mediated signaling is due to the simultaneous binding of the multispecific molecule to IL-4R and CD63 and the consequent internalization and degradation of the entire antibody-IL-4R-CD63 complex.

Figure 5:
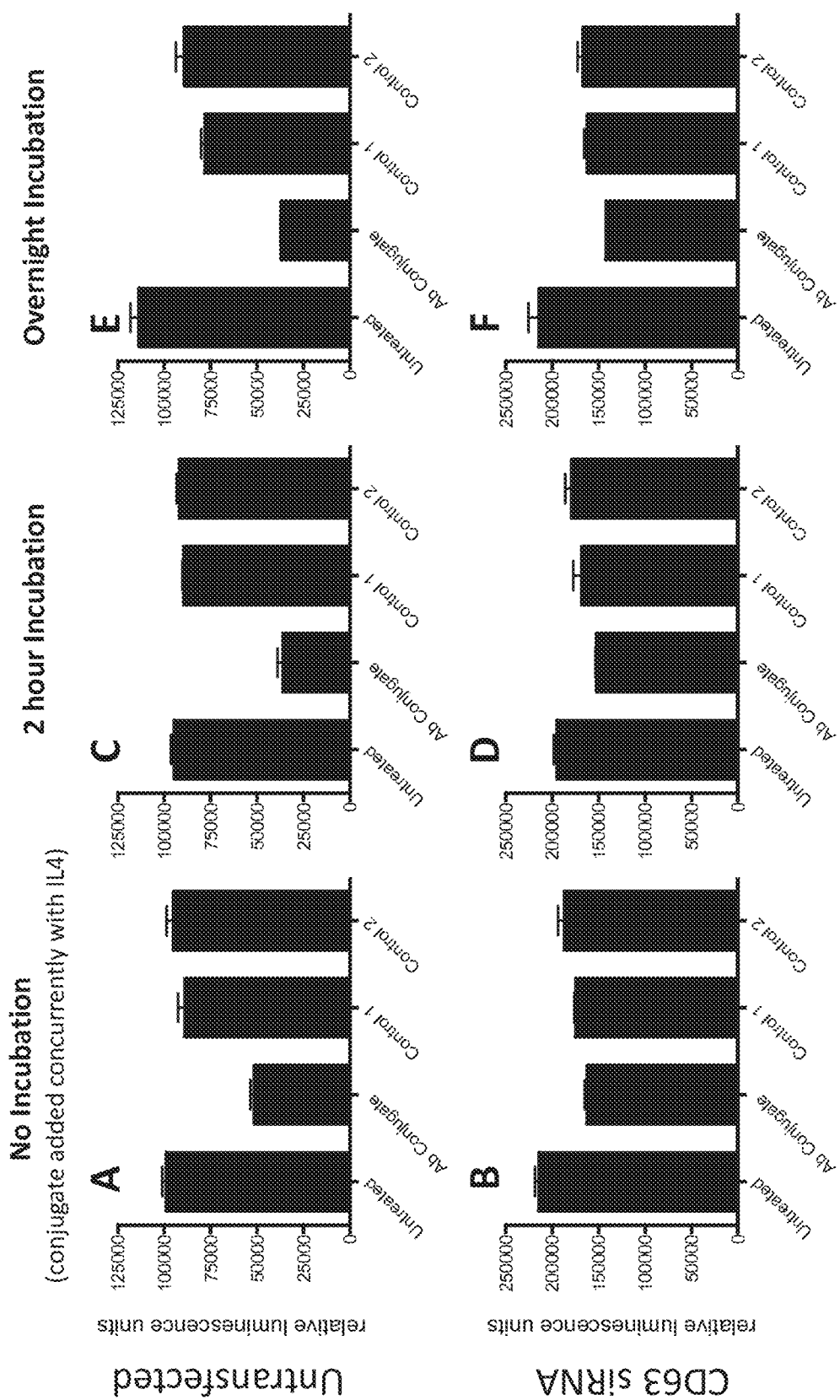
FIG. 5 shows the results of an experiment carried out in a similar manner as the experiments shown in FIGS. 3 and 4, except that the reporter cells were incubated with the multispecific antigen binding protein ("Ab conjugate") or control constructs ("control 1" and "control 2") for 2 hours or overnight prior to the addition of IL-4 ligand. The top row of bar graphs represent the results of experiments conducted in cells expressing normal levels of CD63 ("untransfected"), while the bottom row of bar graphs represents the results of experiments conducted in cells in which CD63 expression was significantly reduced in the reporter cell line by an siRNA directed against CD63.

Similar experiments were next carried out in which the anti-IL-4R/anti-CD63 multispecific molecule, or the control constructs, were allowed to incubate with the HEK293/STAT6-luc reporter cell line for various amounts of time prior to the addition of IL-4. In a first set of such experiments, the molecules were allowed to incubate with the reporter cell line for 0 hours (i.e., added concurrently with IL-4), 2 hours, or overnight prior to the addition of 50 pM IL-4. Luciferase activity was measured six hours after the addition of IL-4. Results are shown in FIG. 5, top panel ("untransfected"). In a further set of experiments, a similar protocol was carried out, except that the experimental or control molecules were allowed to incubate with the reporter cell line for 15 minutes, 30 minutes, 1 hour or 2 hours prior to the addition of 50 pM IL-4. Results are shown in FIG. 6.

Figure 6:
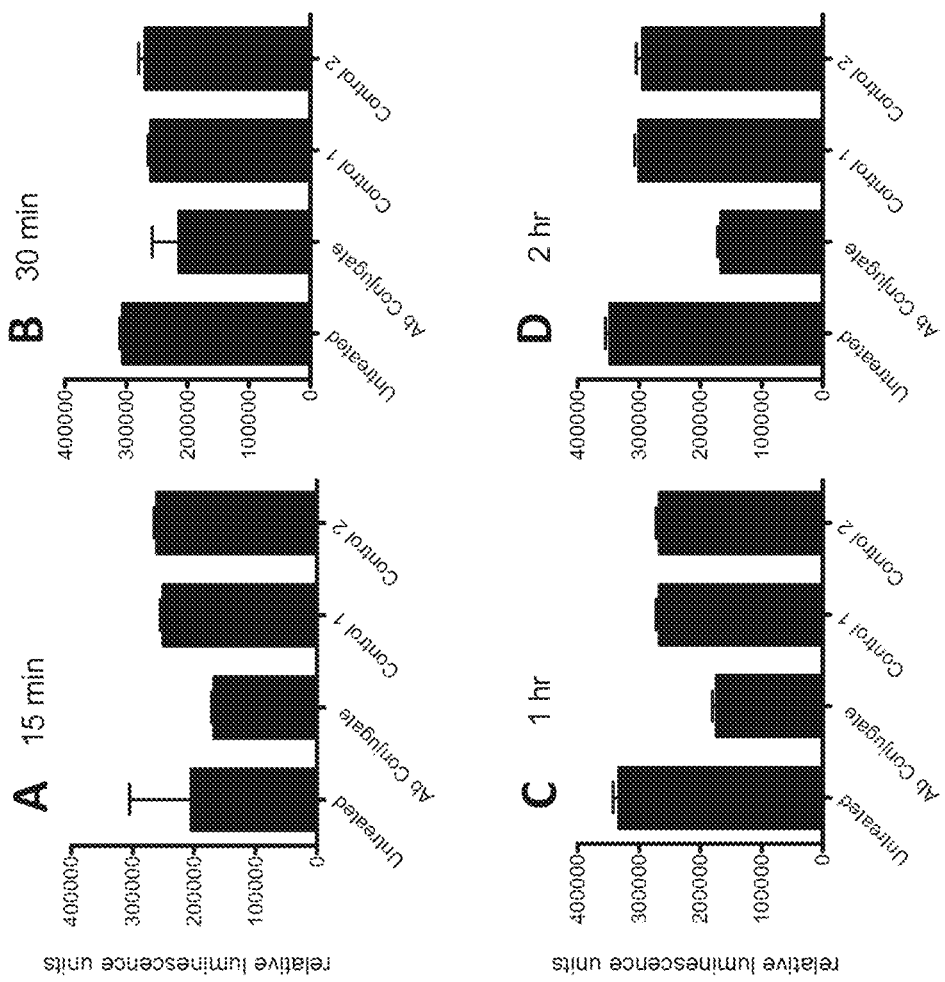
FIG. 6 shows the results of an experiment carried out in a similar manner as the experiments shown in FIGS. 3 and 4, except that the reporter cells were incubated with the anti-IL-4R/anti-CD63 multispecific antigen binding protein ("Ab conjugate") or control constructs ("control 1" and "control 2") for 15 minutes, 30 minutes, 1 hour or 2 hours prior to the addition of IL-4 ligand.

The results summarized in FIGS. 5 and 6 show that the anti-IL-4R/anti-CD63 multispecific molecule is able to inhibit IL-4-mediated signaling, and that this inhibitory effect is enhanced with longer incubation times. As with the initial set of experiments, it was confirmed using CD63 siRNA that the inhibitory effect of the anti-IL-4R/anti-CD63 multispecific molecule was dependent on CD63 expression (FIG. 5 bottom panel ["CD63 siRNA"]).

In summary, this Example provides further proof-of-concept for the inhibition of a target molecule activity through the use of a multispecific antigen-binding molecule that is capable of simultaneously binding both the target molecule (in this case IL-4R) and an internalizing effector protein (in this case CD63) to thereby cause the internalization and degradative rerouting of the target molecule within a cell. Stated differently, the simultaneous binding of IL-4R and CD63 by the exemplary multispecific antigen-binding molecule attenuated the activity of IL-4R to a substantially greater extent (i.e., >10%) than the binding of IL-4R by the control constructs alone.

Example 3

An Anti-IL-4R×Anti-CD63 Bispecific Antibody Attenuates IL-4R Activity in a CD63-Dependent Manner The experiments of Example 2, herein, show that an anti-IL-4R/anti-CD63 multispecific molecule inhibits IL-4-mediated signaling in a CD63-dependent manner. In those experiments, the multispecific antigen-binding molecule consisted of two separate monoclonal antibodies (anti-IL-4R and anti-CD63) that were connected via a biotin-streptavidin linkage. To confirm that the results observed with that proof-of-concept multispecific antigen-binding molecule are generalizable to other multispecific antigen-binding molecule formats, a true bispecific antibody was constructed.

Standard bispecific antibody technology was used to construct a bispecific antibody consisting of a first arm specific for IL-4R and a second arm specific for CD63. The IL-4R-specific arm contained an anti-IL-4R heavy chain paired with a CD63-specific light chain. The CD63-specific light chain was paired with the IL-4R specific heavy chain solely for purposes of convenience of construction; nevertheless, the pairing of the anti-IL-4R heavy chain with the anti-CD63 light chain retained full specificity for IL-4R and did not exhibit binding to CD63. The CD63-specific arm contained an anti-CD63 heavy chain paired with an anti-CD63 light chain (the same light chain as used in the IL-4R arm). The anti-IL-4R heavy chain (comprising SEQ ID NO:3) was derived from the full anti-IL-4R antibody as used in Example 2; However, the anti-CD63 heavy and light chains were derived from the anti-CD63 antibody designated H5C6, obtained from the Developmental Studies Hybridoma Bank (University of Iowa Department of Biology, Iowa City, Iowa). As with the full anti-IL-4R antibody used in Example 2, the anti-IL-4R component of the bispecific antibody used in this Example exhibited only moderate IL-4R blocking activity on its own.

Figure 7:
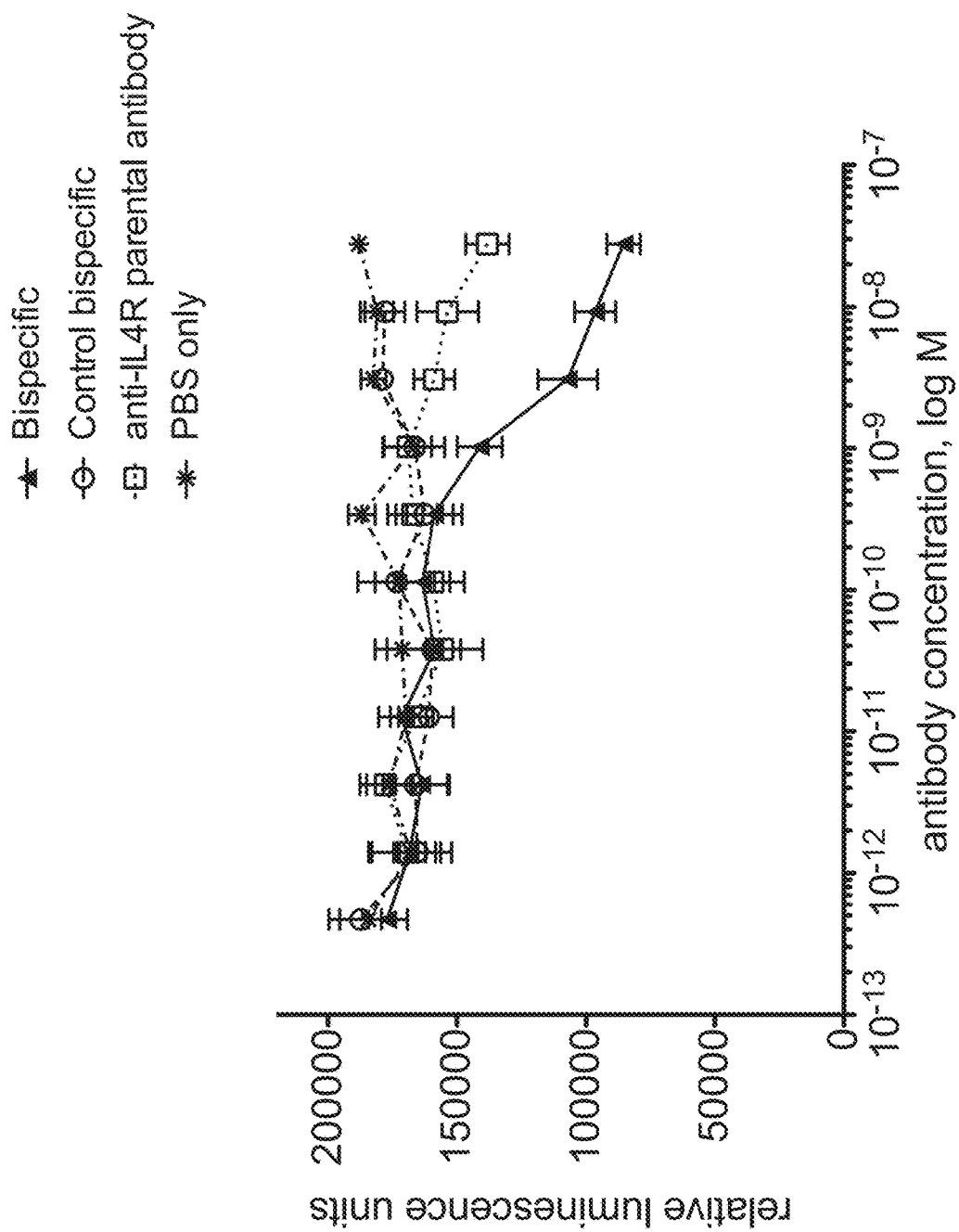
FIG. 7 shows the results of an experiment in which Stat6-luc reporter cells were treated with 10 pM IL-4 in the presence of various dilutions of an anti-IL-4R×anti-CD63 bispecific antibody ("bispecific"), or control constructs (anti-IL-4R monospecific, or mock bispecific that only binds IL-4R).

An IL-4 luciferase assay was carried out to assess the blocking activity of the anti-IL-4R×anti-CD63 bispecific antibody. Briefly, serial dilutions of anti-IL-4R×anti-CD63 bispecific antibody or control molecules were added to HEK293/STAT6-luc reporter cells (see Example 2). Under normal conditions, these cells produce a detectable luciferase signal when treated with IL-4. For this experiment, 10 pM IL-4 was then added to the cells, and luciferase activity was quantified for each dilution of antibody used. The controls used in this assay were: (a) mock bispecific antibody that binds IL-4R with one arm and has a non-functional anti-CD63 arm (i.e., containing one anti-IL-4R heavy chain and one anti-CD63 heavy chain, both paired with the anti-IL-4R light chain); (b) anti-IL-4R monospecific antibody; and (c) buffer (PBS) only (without antibody). Results are shown in FIG. 7. As shown in FIG. 7, for the control samples used, luciferase activity remained relatively high even at the highest antibody concentrations, whereas for the bispecific antibody, luciferase activity declined significantly as antibody concentration increased. These results confirm that simultaneous binding of IL-4R and CD63 by a bispecific antibody causes substantial inhibition of IL-4R activity.

Example 4

Internalization of SOST Using a Multispecific Antigen-Binding Molecule That Simultaneously Binds SOST and CD63

In this Example, the ability of multispecific antigen-binding molecules to promote the internalization of the soluble target molecule SOST (sclerostin) was assessed. For these experiments, the target molecule was a fusion protein consisting of a human SOST protein tagged with a pHrodo™ moiety (Life Technologies, Carlsbad, Calif.) and a myc tag. The pHrodo™ moiety is a pH-sensitive dye that is virtually non-fluorescent at neutral pH and brightly fluorescent in an acidic environment such as the endosome. The fluorescent signal, therefore, can be used as an indicator of cellular internalization of the SOST fusion protein. The multispecific antigen-binding molecules for these experiments were bispecific antibodies with binding specificity for both CD63 (an internalizing effector protein) and the SOST fusion protein (a soluble target molecule), as described in more detail below.

The experiments were conducted as follows: Briefly, HEK293 cells were plated at 10,000 cells/well in poly-D-lysine coated 96 well plates (Greiner Bio-One, Monroe, N.C.). After allowing the cells to settle overnight, the media was replaced with media containing antibody (5 µg/mL, as described below), pHrodo™-myc-tagged-SOST (5 µg/mL), heparin (10 µg/mL), and Hoechst 33342. The cells were then incubated for either 3 hours on ice or 3 hours at 37° C. All cells were washed twice prior to imaging in PBS, and the number of fluorescent spots per cell, as well as the corresponding fluorescence intensity, was counted to establish the extent of pHrodo-myc-tagged-SOST cellular internalization in the presence of the various antibody constructs.

The antibodies used in this Example were as follows: (1) anti-CD63 monospecific antibody (clone H5C6, Developmental Studies Hybridoma Bank, University of Iowa Department of Biology, Iowa City, Iowa); (2) anti-myc antibody (clone 9E10, Schiweck et al., 1997, FEBS Lett. 414(1):33-38); (3) anti-SOST antibody (an antibody having the heavy and light chain variable regions of the antibody designated "Ab-B" in U.S. Pat. No. 7,592,429); (4) anti-CD63×anti-myc bispecific antibody (i.e., a multispecific antigen-binding molecule comprising an anti-CD63 arm derived from the antibody H5C6 and an anti-myc arm derived from 9E10); (5) anti-CD63×anti-SOST bispecific antibody #1 (i.e., a multispecific antigen-binding molecule comprising an anti-CD63 arm derived from the antibody H5C6 and an anti-SOST arm derived from "Ab-B"); and (6) anti-CD63×anti-SOST bispecific antibody #2 (i.e., a multispecific antigen-binding molecule comprising an anti-CD63 arm derived from the antibody H5C6 and an anti-SOST arm derived from the antibody designated "Ab-20" in U.S. Pat. No. 7,592,429). The bispecific antibodies used in these experiments were assembled using the so-called "knobs-into-holes" methodology (see, e.g., Ridgway et al., 1996, Protein Eng. 9(7):617-621).

Figure 8:
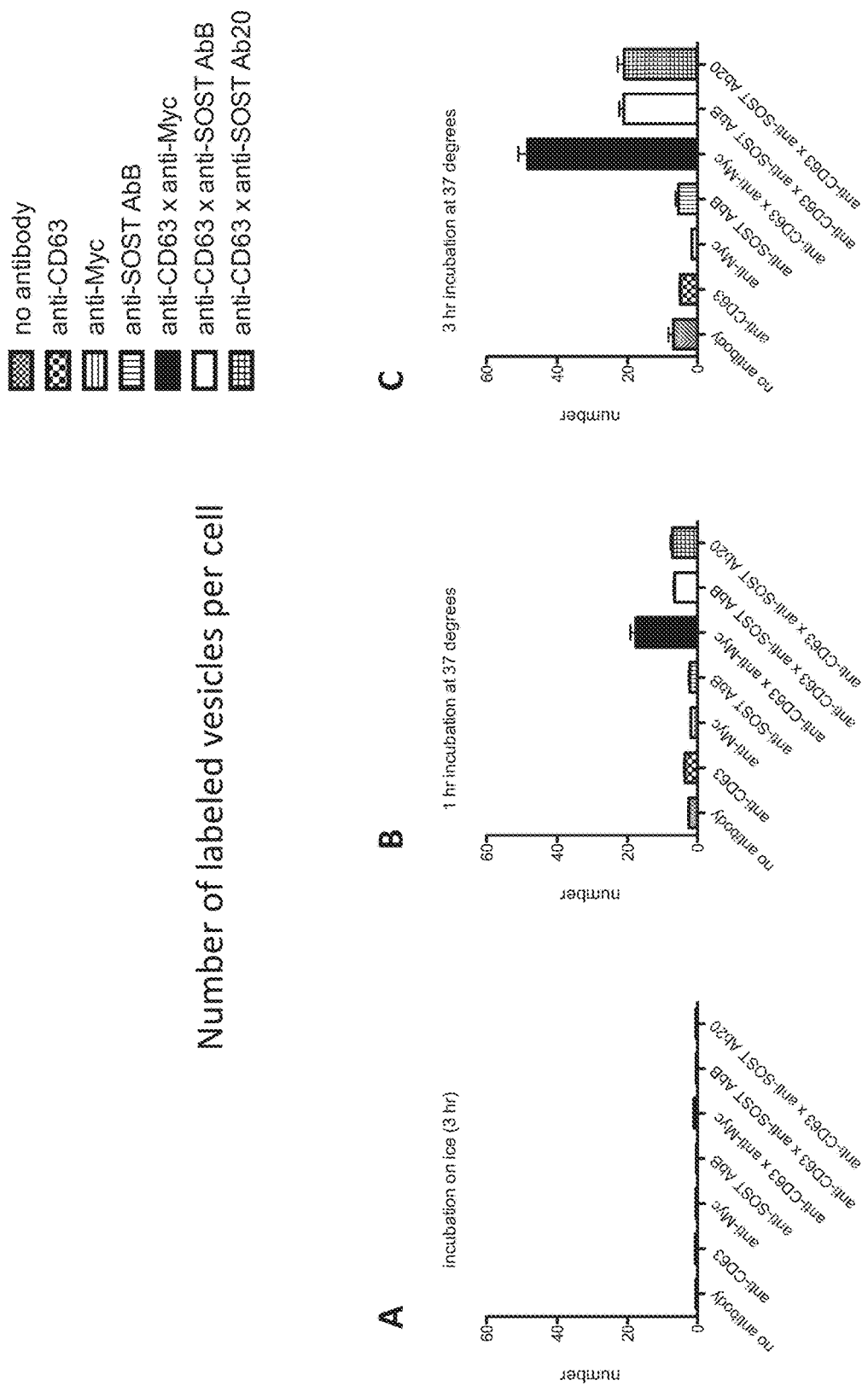
FIG. 8 shows the results of experiments in which HEK293 cells were treated with a SOST construct labeled with a myc tag and a pH-sensitive label (that produces a fluorescent signal at low pH), along with the various mono-specific and bispecific antibodies as shown. Results are expressed in terms of number of fluorescent spots (i.e., labeled vesicles) per cell. Panel A shows the results following incubation on ice for 3 hours, panel B shows the results following 1 hour incubation at 37° C., and panel C shows the results following 3 hours incubation at 37° C.

Results of the internalization experiments are shown in FIG. 8. FIG. 8 shows the number of spots (labeled vesicles) per cell, under the various treatment conditions tested. Taken together, the results of these experiments demonstrate that the bispecific constructs, which simultaneously bind CD63 and SOST (either directly or via the myc tag), caused the greatest amount of SOST internalization as reflected by the fluorescence intensity and number of fluorescent spots per cell over time at 37° C. Thus, the multispecific antigen-binding molecules used in this Example are able to effectively direct the internalization of a soluble target molecule.

Example 5

Changes in Bone Mineral Density in Mice Treated with A Multispecific Antigen-Binding Molecule that Binds CD63 and SOST An anti-CD63×anti-SOST multispecific antigen-binding molecule, as described in Example 4, is next tested for its ability to increase bone mineral density in mice. Five groups of mice (about 6 mice per group) are used in these experiments. The treatment groups are as follows: (I) untreated negative control mice; (II) mice treated with a blocking anti-SOST monospecific antibody that is known to increase bone mineral density on its own (positive control); (III) mice treated with a bispecific antibody that specifically binds CD63 and SOST but does not inhibit SOST activity on its own or only slightly inhibits SOST activity on its own; (IV) mice treated with an anti-CD63 parental antibody (i.e., a monospecific antibody containing the same anti-CD63 antigen-binding domain as in the bispecific antibody); and (V) mice treated with an anti-SOST parental antibody (i.e., a monospecific antibody containing the same anti-SOST antigen-binding domain as in the bispecific antibody). The amount of antibody administered to the mice in each group is about 10 to 25 mg/kg.

It is expected that mice in group III (treated with an anti-SOST×anti-CD63 bispecific antibody) will exhibit an increase in bone mineral density that is at least comparable to that which is observed in the mice of group II (treated with a known blocking anti-SOST antibody), even though the anti-SOST component of the bispecific antibody does not inhibit SOST activity on its own (as confirmed by the mice in Group V which are expected to not exhibit an increase in bone mineral density). The increase in bone mineral density that is expected in the mice of group III is believed to be driven by CD63-mediated internalization of SOST, as observed in the cellular experiments of Example 4, above.

Example 6

Cellular Internalization of Lipopolysaccharide (LPS) Mediated by a Multispecific Antigen-Binding Molecule That Simultaneously Binds LPS and CD63

This Example illustrates the use of a multispecific antigen-binding molecule of the invention to direct the internalization of a non-protein target molecule, namely lipopolysaccharide (LPS). LPS is a component of the outer membrane of Gram-negative bacteria and is known to contribute to septic shock. Anti-LPS antibodies have been investigated as possible treatment agents for sepsis. The experiments of the present Example were designed to assess the ability of a multispecific antigen-binding molecule to promote the internalization of LPS.

The multispecific antigen-binding molecule used in this Example was a bispecific antibody with one arm directed to LPS (target) and the other arm directed to CD63 (internalizing effector protein). The anti-LPS arm was derived from the antibody known as WN1 222-5. (DiPadova et al., 1993, *Infection and Immunity* 61(9):3863-3872; Muller-Loennies et al., 2003, *J. Biol. Chem.* 278(28):25618-25627; Gomery et al., 2012, *Proc. Natl. Acad. Sci* USA 109(51):20877-20882; U.S. Pat. No. 5,858,728). The anti-CD63 arm was derived from the H5C6 antibody (see Example 4). The anti-LPS×anti-CD63 bispecific antibody (i.e., multispecific antigen-binding molecule) was assembled using the so-called "knobs-into-holes" methodology (see, e.g., Ridgway et al., 1996, Protein Eng. 9(7):617-621).

Two LPS species were used in these experiments: *E. coli* LPS and *Salmonella minnesota* LPS. Both versions were obtained as fluorescent-labeled molecules (ALEXA-FLUORO-488-labeled LPS, Life Technologies, Carlsbad, Calif.).

Experiments were conducted as follows: HEK293 cells were plated in 96-well PDL-coated imaging plates. After overnight rest, media was replaced with fresh medium. Fluorescently labeled LPS (either *E. coli*- or *S. minnesota*-derived) was added in regular medium. Next, the anti-LPS× anti-CD63 bispecific antibody, or control half-antibodies paired with dummy Fc, were added to the samples. Following various incubation times at 37° C. (1 hour and 3 hours) or on ice (3 hours), cells from the LPS-treated samples were processed as follows: washed—quenched with anti-ALEXA-FLUOR®-488 antibody—washed & fixed. The anti-ALEXA-FLUORO-488 antibody quenches fluorescence from non-internalized (i.e., surface bound) fluorophore. Thus, any fluorescence observed in the quenching antibody-treated samples is due to internalized LPS. The level of fluorescence from each sample at the various time points was measured.

Figure 9:
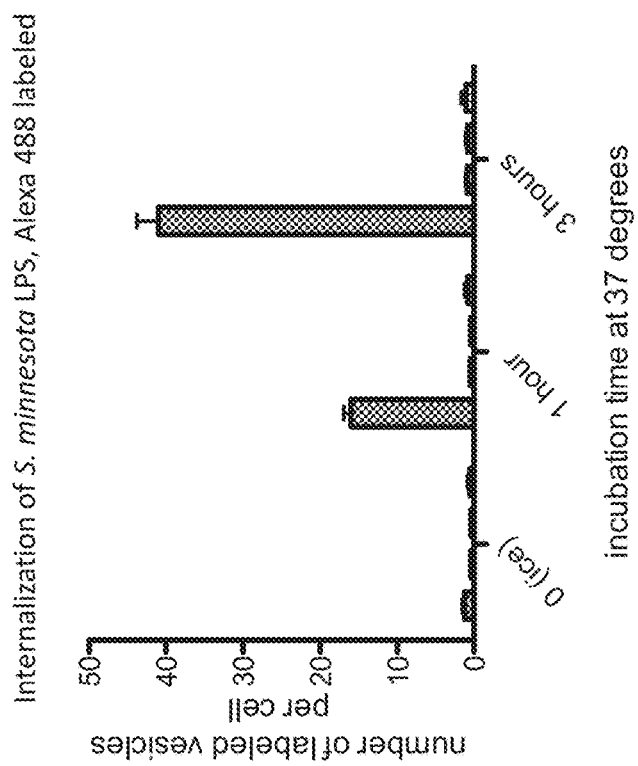
FIG. 9 shows the results of experiments in which HEK293 cells were treated with fluorescently-labeled lipopolysaccharide (LPS) from *E. coli* (Panel A) or *S. minnesota* (Panel B), along with an anti-CD63×anti-LPS bispecific antibody, control antibodies, or LPS only, for various times, followed by quenching of non-internalized (i.e., surface bound) fluorophore. Fluorescent signal therefore reflects internalized LPS under the various conditions shown. Results are expressed in terms of number of fluorescent spots (i.e., labeled vesicles) per cell.
Figure 9:
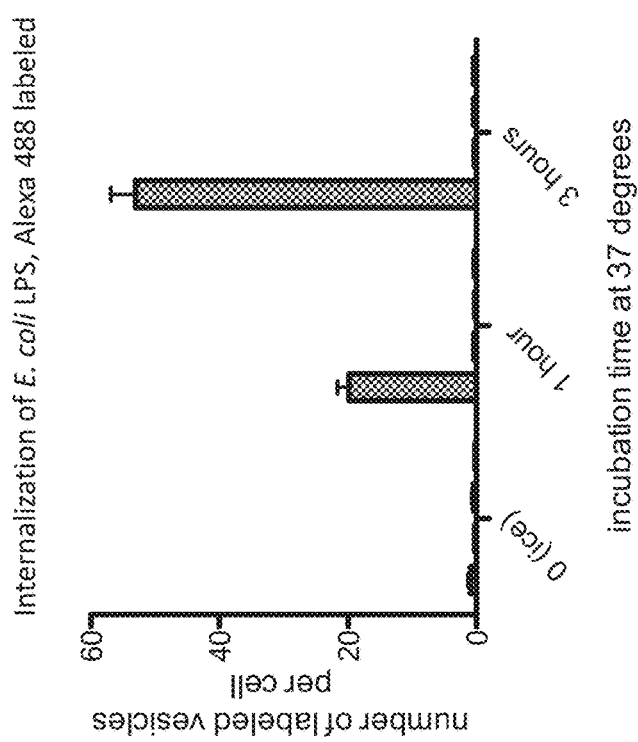

FIG. 9 expresses the results of these experiments in terms of the number of labeled vesicles per cell. As shown in FIG. 9, only cells treated with the anti-CD63×anti-LPS bispecific antibody demonstrated significant numbers of labeled vesicles that increased over time. Cells treated with labeled LPS and the control antibodies did not exhibit appreciable numbers of fluorescent vesicles, indicating that LPS was not internalized under those treatment conditions.

This Example therefore demonstrates that an anti-LPS× anti-CD63 bispecific antibody causes internalization of LPS into cells in a manner that requires simultaneous binding of LPS and CD63. Accordingly, these results support the use of multispecific antigen-binding molecules of the invention to promote cellular internalization of target molecules such as LPS for the treatment of diseases and disorders such as sepsis.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. A multispecific antigen-binding molecule comprising:
a first antigen-binding domain (D1); and
a second antigen-binding domain (D2);
wherein D1 is an antigen-binding portion of an antibody that binds a target molecule (T);
wherein D2 is an antigen-binding portion of an antibody that binds an internalizing effector protein (E);
wherein T is IL-4R, SOST, or LPS;
wherein E is CD63;
wherein D2 binds E with lower affinity than D1 binds T such that the multispecific antigen-binding molecule preferentially targets T; and
wherein binding of both T and E by the multispecific antigen-binding molecule results in the internalization and degradation of T through its physical linkage to E.

2. The multispecific antigen-binding molecule of claim 1, wherein T is a cell surface-expressed target molecule.

3. The multispecific antigen-binding molecule of claim 1, wherein T is a soluble target molecule.

4. The multispecific antigen-binding molecule of claim 1, wherein D1 and/or D2 exhibits pH-dependent binding to its antigen.

5. The multispecific antigen-binding molecule of claim 4, wherein D1 binds T with lower affinity at acidic pH as compared to neutral pH; and/or wherein D2 binds E with lower affinity at acidic pH as compared to neutral pH.

6. The multispecific antigen-binding molecule of claim 1, wherein D1 and/or D2 comprise(s) a heavy chain variable region (HCVR) and a light chain variable region (LCVR).

7. The multispecific antigen-binding molecule of claim 6, wherein the multispecific antigen-binding molecule is a bispecific antibody.

8. The multispecific antigen-binding molecule of claim 1, wherein the multispecific antigen-binding molecule is conjugated to a drug, toxin, or radioisotope.

9. The multispecific antigen-binding molecule of claim 8, wherein the multispecific antigen-binding molecule is conjugated to a cytotoxic drug selected from the group consisting of calicheamicin, esperamicins, methotrexate, doxorubicin, melphalan, chlorambucil, ara-C, vindesine, mitomycin C, cis-platinum, etoposide, bleomycin, 5-fluorouracil, estramustine, vincristine, paclitaxel, larotaxel, tesetaxel, orataxel, docetaxel, dolastatin 10, auristatin E, auristatin PHE, and maytansine-based compounds.

10. The multispecific antigen-binding molecule of claim 9, wherein the cytotoxic drug is selected from the group consisting of calicheamicin, an auristatin, and maytansine-based compounds.

11. A method of forcing the internalization and degradation of a target (T) expressed on the surface of a cell comprising the step of physically linking T to an internalizing effector protein (E) by contacting the cell with the multispecific antigen-binding molecule of claim 1.

12. The method of claim 11, wherein T is IL-4R.

13. The method of claim 11, wherein T is SOST.

14. The method of claim 11, wherein T is LPS.

* * * * *